(12) United States Patent
Kono et al.

(10) Patent No.: US 12,175,664 B2
(45) Date of Patent: Dec. 24, 2024

(54) IMAGE RECORDING APPARATUS, INFORMATION PROCESSING APPARATUS, INFORMATION PROCESSING METHOD, AND RECORDING MEDIUM

(71) Applicant: OLYMPUS CORPORATION, Tokyo (JP)

(72) Inventors: Takashi Kono, Hachioji (JP); Yamato Kanda, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 385 days.

(21) Appl. No.: 17/550,513

(22) Filed: Dec. 14, 2021

(65) Prior Publication Data
US 2022/0108448 A1 Apr. 7, 2022

Related U.S. Application Data

(63) Continuation of application No. PCT/JP2019/023977, filed on Jun. 17, 2019.

(51) Int. Cl.
| | | |
|---|---|---|
| *G06T 7/00* | (2017.01) | |
| *G06T 7/20* | (2017.01) | |
| *G16H 30/20* | (2018.01) | |
| *G16H 30/40* | (2018.01) | |
| *G16H 50/20* | (2018.01) | |

(52) U.S. Cl.
CPC .............. *G06T 7/0012* (2013.01); *G06T 7/20* (2013.01); *G16H 30/20* (2018.01); *G16H 30/40* (2018.01); *G16H 50/20* (2018.01); *G06T 2207/10068* (2013.01); *G06T 2207/20081* (2013.01); *G06T 2207/20084* (2013.01); *G06T 2207/30096* (2013.01)

(58) Field of Classification Search
None
See application file for complete search history.

(56) References Cited

U.S. PATENT DOCUMENTS

| | | | | |
|---|---|---|---|---|
| 2011/0245660 | A1* | 10/2011 | Miyamoto | .............. G06T 15/08 382/128 |
| 2012/0095331 | A1 | 4/2012 | Ohashi | |

(Continued)

FOREIGN PATENT DOCUMENTS

| | | |
|---|---|---|
| JP | 2002-200048 A | 7/2002 |
| JP | 2006-167289 A | 6/2006 |

(Continued)

OTHER PUBLICATIONS

International Search Report dated Aug. 27, 2019 received in PCT/JP2019/023977.
English abstract only of WO 2005/001742 A2.

*Primary Examiner* — Leon Flores
(74) *Attorney, Agent, or Firm* — Scully, Scott, Murphy & Presser, P.C.

(57) ABSTRACT

An information processing apparatus includes a processor. The processor acquires a medical image, identifies the acquired medical image and acquires an identification result, analyzes a motion relating to interpretation of the medical image by a user to acquire a motion analysis result, and compares the identification result and the motion analysis result and acquires a comparison result relating to coincidence or noncoincidence of the identification result and the motion analysis result.

31 Claims, 18 Drawing Sheets

(56) References Cited

U.S. PATENT DOCUMENTS

| | | |
|---|---|---|
| 2013/0198200 A1 | 8/2013 | Takei |
| 2018/0137244 A1 | 5/2018 | Sorenson et al. |

FOREIGN PATENT DOCUMENTS

| | | |
|---|---|---|
| JP | 2006-301965 A | 11/2006 |
| JP | 2007-528746 A | 10/2007 |
| JP | 2008-036262 A | 2/2008 |
| JP | 2008-234309 A | 10/2008 |
| JP | 2009-082441 A | 4/2009 |
| JP | 2009-086750 A | 4/2009 |
| JP | 2012-088828 A | 5/2012 |
| JP | 5048286 B2 | 10/2012 |
| JP | 2013-039230 A | 2/2013 |
| JP | 2013-041428 A | 2/2013 |
| JP | 2013-149265 A | 8/2013 |
| JP | 2013-176538 A | 9/2013 |
| JP | 2014-048823 A | 3/2014 |
| JP | 2014-104293 A | 6/2014 |
| JP | 2016-105796 A | 6/2016 |
| JP | 2017-010577 A | 1/2017 |
| JP | 2017-074363 A | 4/2017 |
| JP | 2017-086685 A | 5/2017 |
| JP | 2018-110040 A | 7/2018 |

\* cited by examiner

IMAGE RECORDING APPARATUS, INFORMATION PROCESSING APPARATUS, INFORMATION PROCESSING METHOD, AND RECORDING MEDIUM

CROSS REFERENCE TO RELATED APPLICATION

This application is a continuation application of PCT/JP2019/023977 filed on Jun. 17, 2019, the entire contents of which are incorporated herein by this reference.

BACKGROUND OF THE INVENTION

1. Field of the Invention

The present invention relates to an image recording apparatus, an information processing apparatus, an information processing method, and a recording medium.

2. Description of the Related Art

In image diagnosis in a medical field, various systems for photographing medical images of various anatomical structures relating to respective patients have been developed in order to classify and evaluate disease conditions. As these photographing systems, for example, an endoscope system, a CT (computer tomography) system, an MRI (magnetic resonance imaging) system, an X ray system, an ultrasound system, and a PET (positron-emission tomography) system are known.

Japanese Patent Application Laid-Open Publication No. 2007-528746 discloses a method of machine-learning annotation data by medical personnel such as a doctor to thereby realize a lesion detecting function by CADe/x (computer-aided detection/diagnosis), which is so-called computer detection/diagnosis support.

In order to improve the performance of an identifier by the machine learning explained above, in general, a large amount of data are necessary. Therefore, in a system requiring the identifier to perform the machine learning, it is predicted that an amount of data to be handled will increase. However, since the large amount of data necessitates an enormous recording capacity and occupies a network line in transfer of the data, it is predicted that more "efficient data collection" will be necessary in the future. As this "efficient data collection", for example, it is conceivable that only "a medical image reflecting a target, identification by the machine learning of which the identifier is not good at" is collected as useful data.

As a technique for selecting a useful medical image from a large amount of medical images, for example, Japanese Patent No. 5048286 discloses a technique for efficiently transferring only a medical image obtained by photographing a desired site out of a plurality of medical images.

SUMMARY OF THE INVENTION

An information processing apparatus according to an aspect of the present invention includes a processor, the processor being configured to: acquire a medical image; identify the acquired medical image and acquire an identification result; analyze a motion relating to interpretation of the medical image by a user to acquire a motion analysis result; and compare the identification result and the motion analysis result and acquire a comparison result relating to coincidence or noncoincidence of the identification result and the motion analysis result.

An image recording apparatus according to an aspect of the present invention includes a processor, the processor being configured to: acquire a medical image; identify the acquired medical image and acquire an identification result; analyze a motion relating to interpretation of the medical image by a user to acquire a motion analysis result; compare the identification result and the motion analysis result and acquire a comparison result relating to coincidence or noncoincidence of the identification result and the motion analysis result; and store the medical image and information relating to the acquired comparison result.

An information processing method according to an aspect of the present invention includes: acquiring a medical image; identifying the acquired medical image and acquiring an identification result; analyzing a motion relating to interpretation of the medical image by a user to acquire a motion analysis result; and comparing the identification result and the motion analysis result and acquiring a comparison result relating to coincidence or noncoincidence of the identification result and the motion analysis result.

A computer-readable non-transitory recording medium recording an information processing program according to an aspect of the present invention, the information processing program causing a computer to execute: processing for acquiring a medical image; processing for identifying the acquired medical image and acquiring an identification result; processing for analyzing a motion relating to interpretation of the medical image by a user to acquire a motion analysis result; and processing for comparing the identification result and the motion analysis result and acquiring a comparison result relating to coincidence or noncoincidence of the identification result and the motion analysis result.

DETAILED DESCRIPTION OF THE PREFERRED EMBODIMENTS

Embodiments of the present invention are explained below with reference to the drawings.

First Embodiment

Figure 1:
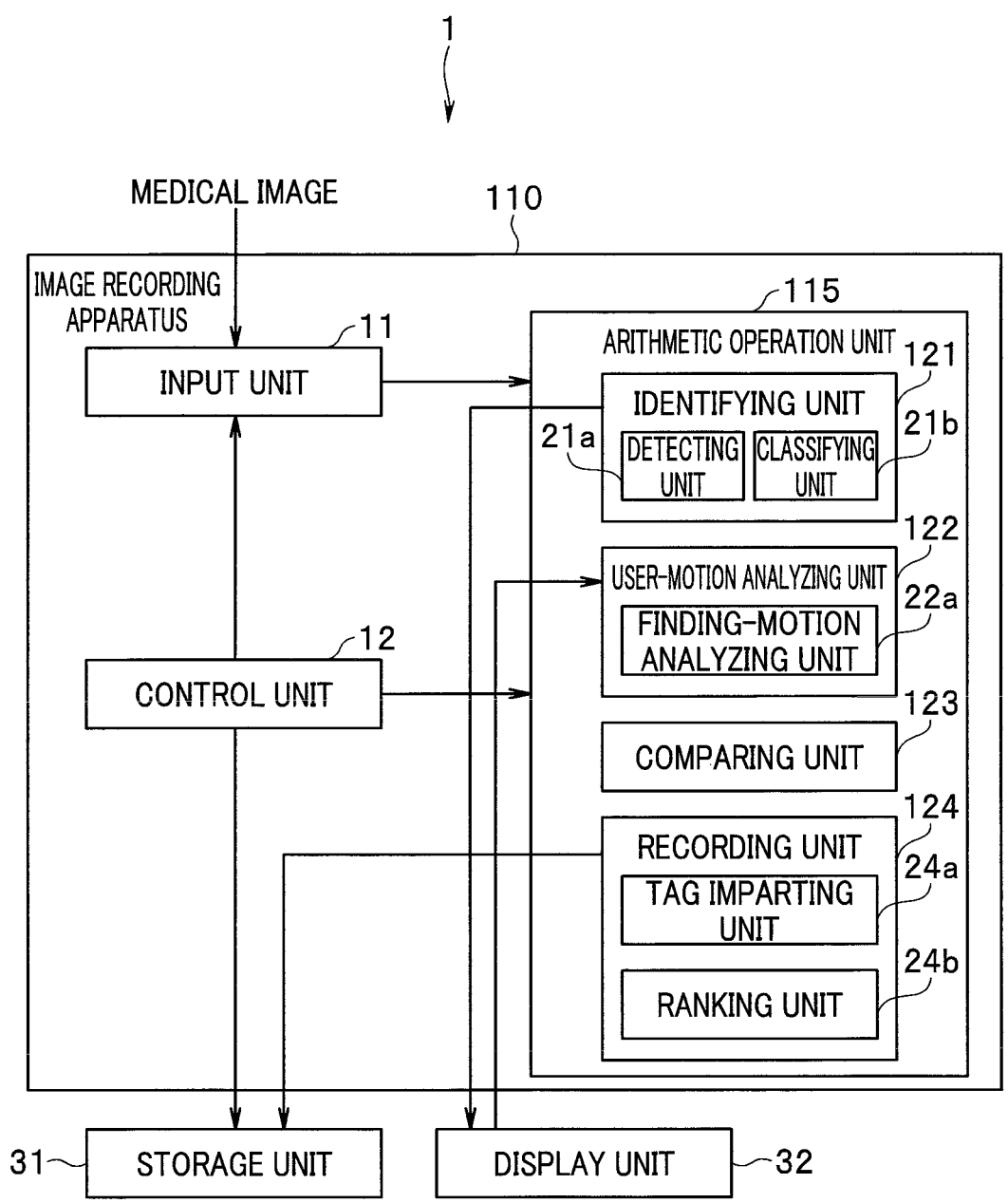
FIG. 1 is a block diagram showing a configuration of a medical system including an image recording apparatus according to a first embodiment of the present invention.
Figure 2:
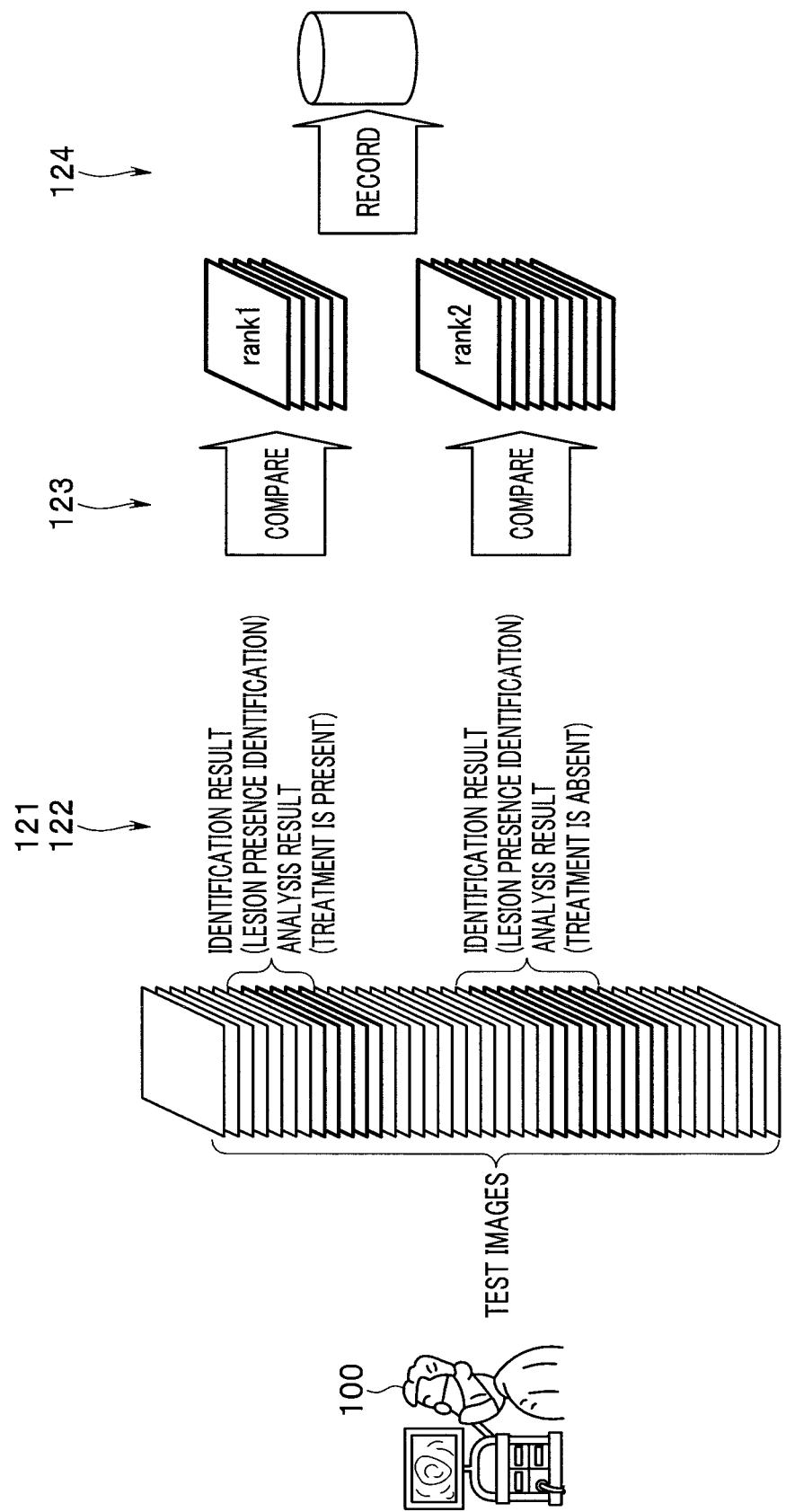
FIG. 2 is an explanatory diagram for explaining an overview of action of the image recording apparatus in the first embodiment.
Figure 3:
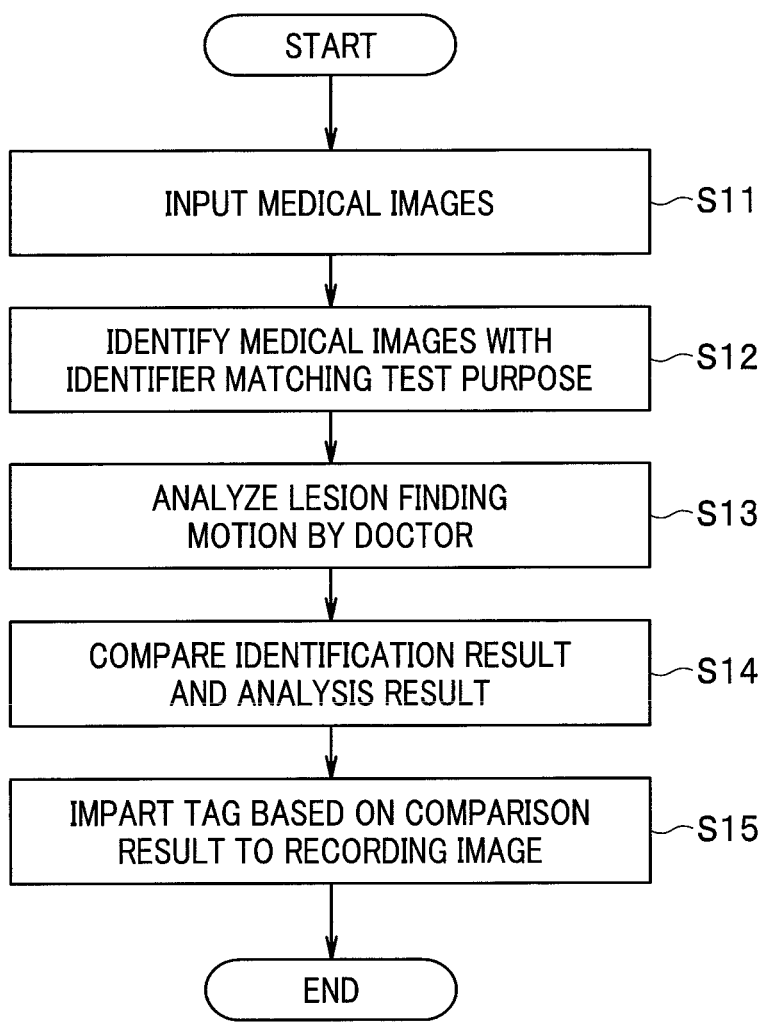
FIG. 3 is a flowchart showing the action of the image recording apparatus in the first embodiment.

FIG. 1 is a block diagram showing a configuration of a medical system including an image recording apparatus (information processing apparatus) according to a first embodiment of the present invention. FIG. 2 is an explanatory diagram for explaining an overview of action of the image recording apparatus in the first embodiment. FIG. 3 is a flowchart showing the action of the image recording apparatus in the first embodiment.

As shown in FIG. 1, a medical system 1 including an image recording apparatus 110 in the first embodiment mainly includes the image recording apparatus 110 configured to acquire a medical image and apply predetermined image processing to the medical image, a storage unit 31 connected to the image recording apparatus 110 and configured to store predetermined data, and a display unit 32 configured to display the medical image to which the image processing is applied in the image recording apparatus 110.

Note that the medical system 1 may be a system including various peripheral apparatuses relating to diagnoses and treatments besides an endoscope including an image pickup unit configured to pick up the medical image and a light source apparatus configured to supply predetermined illumination light to the endoscope or may be a system configuring a part of a network system widely used in a medical site and the like, the network system sharing patient information and the like including medical images and performing medical jobs.

The medical image in the present invention mainly indicates images (for example, an endoscopic image, an ultrasound test image, and a picked-up image) acquired by a doctor, who is a user, himself or herself, using predetermined medical equipment (various image pickup apparatuses such as a medical endoscope apparatus and a medical ultrasound test apparatus) according to an order (medical care policy or the like) of the doctor.

The medical image may be image information formally approved as an image acquired by a predetermined medical practitioner or the like based on a prescribed setting or format in response to an order (request, instruction, or the like) of the doctor. Note that the medical practitioner or the like indicates medical-related various qualified people (so-called medical staff) including a doctor, a nurse, and various expert engineers.

The image recording apparatus 110 mainly includes an input unit 11 connected to, for example, the endoscope explained above and configured to acquire a medical image picked up in an image pickup unit in the endoscope, a control unit 12 configured to control an operation of the entire image recording apparatus 110, and an arithmetic operation unit 115 configured to execute various kinds of processing explained below on the medical image acquired in the input unit 11. Note that, in the present embodiment, the image recording apparatus 110 includes a not-shown memory configured to store various programs and the like besides a not-shown image processing unit configured to apply predetermined image processing to the acquired medical image.

The input unit 11 acquires an endoscopic image (medical image) picked up in, for example, an image pickup unit in a medical endoscope. Note that, as explained above, the medical image is not limited to the endoscopic image and may be, for example, an image acquired using other medical equipment (various image pickup apparatuses such as an ultrasound test apparatus).

The control unit 12 is realized by hardware such as a CPU and reads various programs stored in the memory explained above to thereby perform, according to image data relating to a medical image inputted from the input unit 11, an operation signal inputted from a predetermined input operation unit, or the like, an instruction, data transfer, and the like to respective units configuring the image recording apparatus 110 and collectively controls an operation of the entire image recording apparatus 110.

The arithmetic operation unit 115 includes various circuits, an identifying unit (identifying apparatus) 121, a user-motion analyzing unit 122, a comparing unit 123, and a recording unit 124 characterizing the present invention. The arithmetic operation unit 115 is explained in detail below.

The storage unit 31 is an external data storage unit connected to the image recording apparatus 110 and is realized by various memories such as an updatable and recordable flash memory, an information recording medium such as a hard disk, an SSD, or a CD-ROM, a reading apparatus for the information recording medium, or the like. Further, the storage unit 31 may be a file server set in a medical base such as a hospital via a not-shown internal network (network in the hospital).

The display unit 32 is realized by a display apparatus such as an LCD or an EL display and displays the medical image under control by the control unit 12.

Note that, in the present embodiment, the respective units of the image recording apparatus 110 such as the arithmetic operation unit 115 and the control unit 12 explained above may be configured as electronic circuits or may be configured as circuit blocks in an integrated circuit such as an FPGA (field programmable gate array). For example, the units may include one or more processors (CPUs or the like).

Arithmetic Operation Unit 115 in First Embodiment

Subsequently, a detailed configuration of the arithmetic operation unit 115 in the first embodiment is explained.

The arithmetic operation unit 115 includes the identifying unit 121 configured to identify a medical image such as an endoscopic image acquired in the input unit 11 and acquire an identification result, the user-motion analyzing unit 122 configured to analyze a motion relating to interpretation of the medical image by the doctor (user) to acquire a motion analysis result, the comparing unit 123 configured to compare the identification result acquired in the identifying unit 121 and the motion analysis result acquired in the user-motion analyzing unit 122 and acquire a result of the comparison, and the recording unit 124 configured to store the medical image and information relating to the comparison result acquired in the comparing unit 123.

The identifying unit 121 identifies, out of a medical image group such as acquired endoscopic images, according to a test purpose, medical images in which detection or classification of a target is performed. The identifying unit 121 includes, as an identifier for medical images conforming to the test purpose, one or both of a detecting unit 21a or a classifying unit 21b in the present embodiment.

The detecting unit 21a tests, as a test image group, a medical image group such as endoscopic images acquired in the input unit 11 and detects a predetermined abnormal region from the medical image group. The abnormal region is, for example, a region where a predetermined lesion is present. The detecting unit 21a is configured to, for example, when detecting the presence of the predetermined lesion, sends medical images in which the lesion is present to the comparing unit 123 in a later stage as an identification result (see FIG. 2).

The identifying unit 121 may include the classifying unit 21b as an identifier for medical images according to a test purpose or may include both of the detecting unit 21a and the classifying unit 21b. The classifying unit 21b receives an input of the medical image group explained above acquired in the input unit 11 and performs classification corresponding to the test purpose. The classifying unit 21b sends a classification result corresponding to a diagnosis indicator (for example, a pathological diagnosis result or a clinical diagnosis result) toward the comparing unit 123 in the later stage as an identification result with respect to classified medical images.

In this way, the identifying unit 121 identifies, based on the detection result in the detecting unit 21a or the classification result in the classifying unit 21b or both of the detection result and the classification result, according to the test purpose, the medical image group such as endoscopic images acquired in the input unit 11 and sends an identification result to the comparing unit 123.

In the first embodiment, the user-motion analyzing unit 122 includes a finding-motion analyzing unit 22a configured to analyze a motion relating to finding of a lesion by the doctor. For example, when the input unit 11 acquires endoscopic images as a medical image group, the finding-motion analyzing unit 22a determines, based on a state of a series of medical image groups or an electric signal acquirable from an endoscope related apparatus, a motion of an "endoscope insertion section" relating to the finding of the doctor for the region to analyzing the motion.

When the endoscope insertion section is inserted into a body cavity of a subject (patient), the finding-motion analyzing unit 22a in the present embodiment analyzes, for example, a motion of the doctor (user) to approach and observe a region of interest (lesion). More specifically, the finding-motion analyzing unit 22a acquires enlargement operation of an endoscope apparatus as signal information to analyze the enlargement operation. As another method, at an enlargement observation time in a display screen outputted from an endoscopic image apparatus, the finding-motion analyzing unit 22a determines presence or absence of information such as a displayed icon to analyze the enlargement operation.

As still another analysis, the finding-motion analyzing unit 22a analyzes whether the doctor has stopped removal when operating the endoscope insertion section. More specifically, the finding-motion analyzing unit 22a performs an analysis of a series of medical image groups and, when determining that a singular point (feature point such as a strong edge or an endpoint of the edge by pixel information) in an image has been continuously grasped for a preset constant time or more, analyzes that the doctor has stopped the removal of the insertion section.

The finding-motion analyzing unit 22a analyzes, based on information relating to the motion of the endoscopic insertion section, an act of the doctor confronting the lesion and sends a result of the analysis to the comparing unit 123 in the later stage (see FIG. 2).

Further, in the present embodiment, the finding-motion analyzing unit 22a analyzes a motion (act) of the doctor based on presence or absence of treatment relating to the endoscope after the finding motion of the lesion. In other words, when the doctor found the lesion, the finding-motion analyzing unit 22a determines whether the doctor executed predetermined treatment (treatment was present or absent) thereafter to thereby analyze whether the doctor performed treatment after finding the lesion (treatment was present) or intentionally left the lesion untouched (or neglected the lesion) (treatment was absent) and sends a result of the analysis to the comparing unit 123 in the later stage (see FIG. 2).

As the analysis for presence or absence of treatment, when a treatment instrument is detected in an image and the treatment instrument is in a specific state (for example, a state in which a snare, a needle, or forceps of the treatment instrument is detected), it is determined that the treatment instrument is detected and "treatment is present".

The comparing unit 123 is configured to compare the identification result of the identification in the identifying unit 121 and the motion analysis result of the analysis in the user-motion analyzing unit 122 and send a result of the comparison to a tag imparting unit 24a in the recording unit 124.

In other words, the comparing unit 123 is configured to acquire the identification result of the identification in the identifying unit 121 (the detecting unit 21a or the classifying unit 21b) (for example, data of a medical image in which the lesion is determined as present (the lesion is present)), acquire the motion analysis result of the analysis in the user-motion analyzing unit 122 (in the present embodiment, the finding-motion analyzing unit 22a) (for example, data of a medical image indicating that the doctor performed predetermined treatment after lesion finding and data of a medical image indicating that the doctor did not perform the treatment), compare the identification result and the motion analysis result, and send a result of the comparison to the tag imparting unit 24a in the recording unit 124.

A modification of the comparing unit 123 is explained with reference to FIG. 4.

Figure 4:
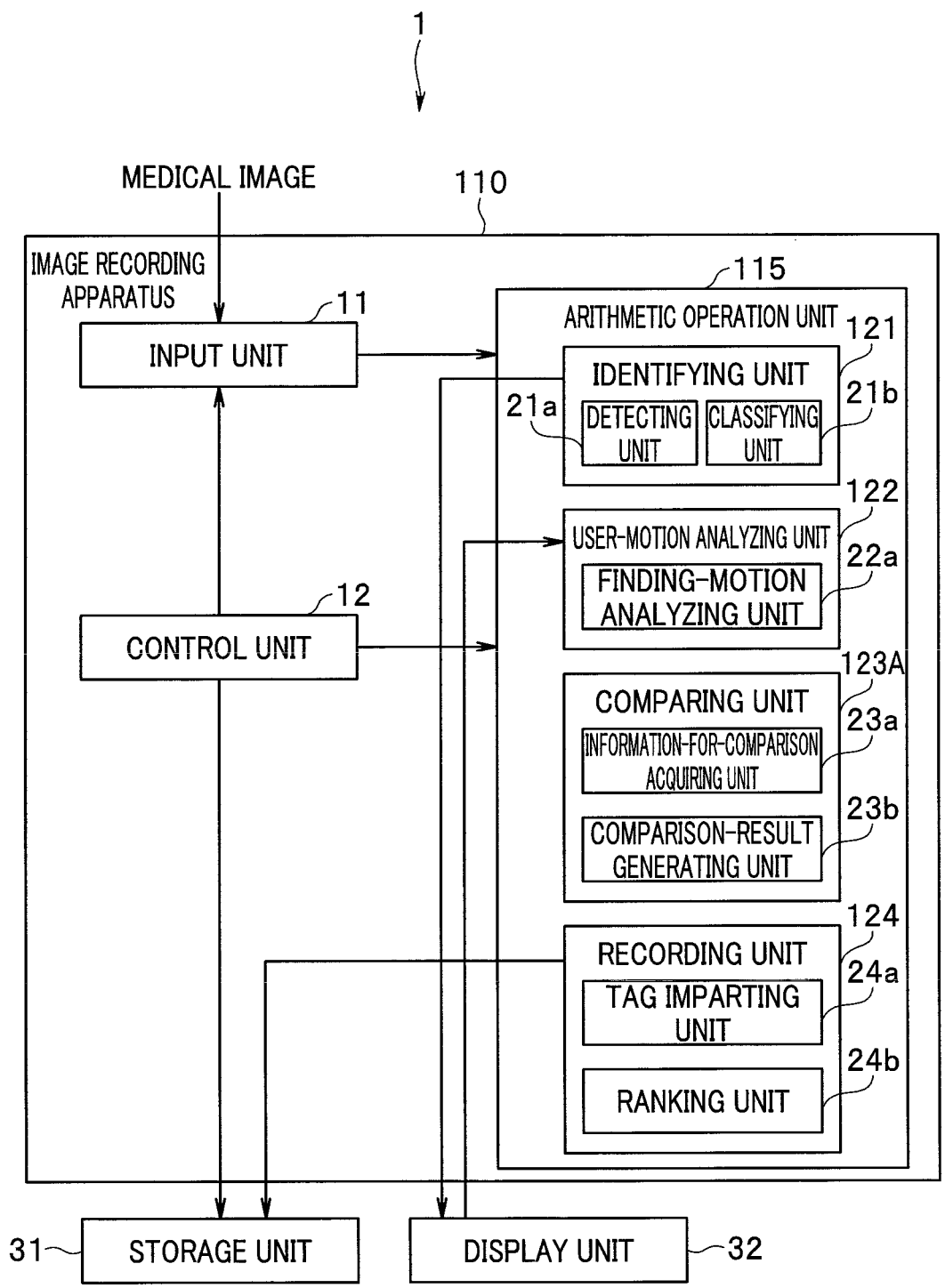
FIG. 4 is a block diagram showing a configuration of a medical system including a modification of the image recording apparatus according to the first embodiment.

As shown in FIG. 4, the comparing unit 123 may be configured as a comparing unit 123A including an information-for-comparison acquiring unit 23a and a comparison-result generating unit 23b. In that case, the information-for-comparison acquiring unit 23a acquires an identification result and a motion analysis result. The comparison-result generating unit 23b compares the identification result and the motion analysis result, generates a result of the comparison, and sends the result of the comparison to the tag imparting unit 24a in the recording unit 124.

Referring back to FIG. 1, a case is considered where the comparing unit 123 compares an identification result in the identifying unit 121 for a certain medical image among a medical image group and a result of the analysis in the user-motion analyzing unit 122 corresponding to the identification result. At this time, for example, when an identification result acquired from the identifying unit 121 relating to the medical image is "a lesion is present" and a result of the analysis acquired from the finding-motion analyzing unit 22a in the user-motion analyzing unit 122 is "treatment is present", assuming that the doctor performed appropriate treatment for a predetermined lesion, the comparing unit 123 regards treatment corresponding to the identification result and a motion (act) of the doctor "coincide" and sends a result of the comparison to the recording unit 124 in a later stage.

In contrast, for example, when an identification result acquired from the identifying unit 121 relating to the medical image is "a lesion is present" and a result of the analysis acquired from the finding-motion analyzing unit 22a in the user-motion analyzing unit 122 is "treatment is absent", assuming that the doctor did not perform appropriate treatment for the predetermined lesion or assuming that treatment by the doctor was unnecessary for the lesion, the comparing unit 123 regards treatment corresponding to the identification result and a motion (act) of the doctor "do not coincide" and sends a result of the comparison to the recording unit 124 in the later stage.

The comparison result in the comparing unit 123 is not limited to a result of choosing between two things of "coincidence" or "noncoincidence" explained above. For example, a case is considered where an identification result in the identifying unit 121 for a medical image group relating to certain constant one group among medical image groups, which are a plurality of test image groups, and a result of the analysis in the user-motion analyzing unit 122 corresponding to the medical image group relating to the certain constant one group are compared. At this time, for example, the comparing unit 123 may send a result of the comparison to the recording unit 124 in the later stage using a degree of "coincidence" or a degree of "noncoincidence" relating to the medical image group of the one group as information concerning constant weighting (for example, weighting of noncoincidence).

The recording unit 124 includes a memory unit configured by a memory such as an updatable and recordable flash memory and includes, in the first embodiment, the tag imparting unit 24a and a ranking unit 24b.

The tag imparting unit 24a generates a tag corresponding to the comparison result acquired in the comparing unit 123 and imparts the tag to medical images relating to the comparison result. The recording unit 124 is configured to store, in the predetermined memory unit explained above, the medical images to which the tag is imparted by the tag imparting unit 24a.

More specifically, based on the comparison result acquired in the comparing unit 123, for example, when both results of the identification result (for example, a lesion is present) of the identification in the identifying unit 121 and the motion analysis result (for example, treatment is present or absent) of the analysis in the finding-motion analyzing unit 22a in the user-motion analyzing unit 122 coincide (in this case, as explained above, "a lesion is present" and "treatment is present"), the tag imparting unit 24a generates a "coincidence tag" indicating coincidence and imparts the "coincidence tag" to the medical images relating to the comparison result.

On the other hand, when the results of the identification result acquired in the identifying unit 121 and the motion analysis result acquired in the finding-motion analyzing unit 22a in the user-motion analyzing unit 122 do not coincide (in this case, as explained above, "a lesion is present" and "treatment is absent"), the tag imparting unit 24a generates a "noncoincidence tag" indicating noncoincidence and imparts the "noncoincidence tag" to the medical images relating to the comparison result.

Note that, without being limited to the generation and the imparting of the "coincidence tag" or the "noncoincidence tag" explained above, the tag imparting unit 24a may generate, based on, for example, comparison result information from the comparing unit 123, a "weighting tag" indicating weight of a noncoincidence degree of the identification result acquired in the identifying unit 121 and the motion analysis result acquired in the finding-motion analyzing unit 22a and impart the "weighting tag" to the medical images relating to the comparison result.

Examples of weighting calculation of the noncoincidence degree include differentiating an importance degree in the noncoincidence tag to be a RANK 1 when "the identification result" indicates that a lesion is absent and "the result of the motion analysis" indicates that treatment is present and to be a RANK 2 when "the identification result" indicates that a lesion is present and "the motion analysis result" indicates that treatment is absent.

In the first embodiment, the recording unit 124 further includes the ranking unit 24b configured to perform, according to the tag generated in the tag imparting unit 24a as explained above, ranking corresponding to a predetermined standard for medical images corresponding to the tag.

The ranking unit 24b performs, according to the tag generated in the tag imparting unit 24a, for example, according to types of the "coincidence tag" and the "noncoincidence tag", predetermined ranking for the medical images corresponding to the tag.

When a "identification result" and a "result of the analysis" for certain medical images coincide (in this case, an identification result acquired from the identifying unit 121 for the medical images is "a lesion is present" and a result of the analysis acquired from the user-motion analyzing unit 122 for the medical images is "treatment is present"), assuming that the doctor performed appropriate treatment for the predetermined lesion, the tag imparting unit 24a generates a "coincidence tag" and imparts the "coincidence tag" to the medical images.

The ranking unit 24b receiving information concerning the "coincidence tag" imparting from the tag imparting unit 24a is configured to rank medical images corresponding to the tag to, for example, a "rank 1" (see FIG. 2) and store the medical images in the predetermined memory unit together with the ranking information "rank 1".

On the other hand, when a "identification result" and an "result of the analysis" for certain medical images do not coincide (in this case, an identification result acquired from the identifying unit 121 for the medical images is "a lesion is present" and a result of the analysis acquired from the user-motion analyzing unit 122 for the medical images is "treatment is absent"), assuming that the doctor did not perform appropriate treatment for the predetermined lesion or assuming that treatment by the doctor is unnecessary for the lesion, the tag imparting unit 24a generates a "noncoincidence tag" and imparts the "noncoincidence tag" to the medical images.

The ranking unit 24b receiving information concerning the "noncoincidence tag" imparting from the tag imparting unit 24a is configured to rank medical images corresponding to the tag to, for example, a "rank 2" (see FIG. 2) and store the medical images in the predetermined memory unit together with the ranking information "rank 2".

The ranking unit 24b may perform, according to the "weighting tag" having the noncoincidence degree explained above generated in the tag imparting unit 24a, predetermined ranking for medical images corresponding to the tag.

In the first embodiment, the recording unit 124 is configured to store the ranked respective medical images in the predetermined memory unit together with the tag information. In other words, the various tags explained above are generated in the tag imparting unit 24a. The respective medical images ranked according to the predetermined standard in the ranking unit 24b according to the generated tags are stored in the predetermined memory unit together with the tag information (for example, the ranking information explained above) (see FIG. 2).

Action of First Embodiment

Subsequently, action of the image recording apparatus in the first embodiment is explained with reference to an explanatory diagram of FIG. 2 and using a flowchart of FIG. 3. FIG. 2 is an explanatory diagram for explaining an overview of action of the image recording apparatus in the first embodiment. FIG. 3 is a flowchart showing the action of the image recording apparatus in the first embodiment.

As shown in FIG. 3, in the image recording apparatus in the first embodiment, first, the input unit 11 acquires predetermined medical images such as endoscopic images (step S11). In the present embodiment, the medical images are assumed to be images (endoscopic images) acquired by a doctor 100 (see FIG. 2), who is a user, himself or herself using predetermined medical equipment (in the present embodiment, a medical endoscope apparatus) according to an order (medical care policy or the like) of the doctor 100.

Subsequently, the identifying unit 121 in the image recording apparatus identifies the medical images such as the endoscopic images acquired in the input unit 11 to match a test purpose and sends the predetermined medical images to the comparing unit 123 as the identification result (step S12).

More specifically, when detecting a predetermined region of interest (for example, a region where a predetermined lesion is present) from a medical image group such as endoscopic images acquired by the input unit 11, the detecting unit 21a in the identifying unit 121 sends presence or absence of a region of interest to the comparing unit 123 as an identification result (see FIG. 2).

The finding-motion analyzing unit 22a in the user-motion analyzing unit 122 analyzes a motion relating to finding of a lesion by the doctor 100 (see FIG. 2) and sends a result of the analysis to the comparing unit 123 (step S13).

When the endoscope insertion section is inserted into a body cavity of a subject (patient), the finding-motion analyzing unit 22a analyzes, for example, a motion for the doctor (user) to approach and observe the region of interest (lesion). More specifically, the finding-motion analyzing unit 22a acquires enlargement operation of the endoscope apparatus as signal information to analyze the enlargement operation. As another method, at an enlargement observation time in a display screen outputted from an endoscopic image apparatus, the finding-motion analyzing unit 22a determines presence or absence of information such as a displayed icon to analyze the enlargement operation.

As still another analysis, the finding-motion analyzing unit 22a analyzes whether the doctor has stopped removal when operating the endoscope insertion section. More specifically, the finding-motion analyzing unit 22a performs an analysis of a series of medical image groups and, when determining that a singular point (feature point such as a strong edge or an endpoint of the edge by pixel information) in an image has been continuously grasped for a preset constant time or more, analyzes that the doctor has stopped the removal of the insertion section.

The finding-motion analyzing unit 22a analyzes, based on information relating to the motion of the endoscopic insertion section, an act of the doctor confronting the lesion and sends a result of the analysis to the comparing unit 123 in the later stage (see FIG. 2).

Further, in the present embodiment, the finding-motion analyzing unit 22a analyzes a motion (act) of the doctor based on presence or absence of treatment relating to the endoscope after the finding motion for the lesion. In other words, the finding-motion analyzing unit 22a determines whether when, the doctor found the lesion, the doctor executed predetermined treatment thereafter to thereby analyze whether the doctor performed treatment after finding the lesion (treatment was present) or intentionally left the lesion untouched (or neglected the lesion) (treatment was absent) and sends a result of the analysis to the comparing unit 123 in the later stage (see FIG. 2).

Subsequently, the comparing unit 123 in the image recording apparatus acquires the identification result of the identification in the identifying unit 121 (the detecting unit 21a or the classifying unit 21b) (for example, data of medical images in which the lesion is determined as present (the lesion is present)) (see FIG. 2), acquires the motion analysis result acquired in the user-motion analyzing unit 122 (for example, data of medical images indicating that the doctor performed predetermined treatment after lesion finding and data of medical images indicating that the doctor did not perform the treatment) (see FIG. 2), compares the identification result and the motion analysis result (see FIG. 2), and sends a result of the comparison to the tag imparting unit 24a in the recording unit 124 (step S14).

More specifically, when an identification result acquired from the identifying unit 121 relating to the medical images is "a lesion is present" and when a result of the analysis acquired from the finding-motion analyzing unit 22a in the user-motion analyzing unit 122 is "treatment is present", assuming that the doctor performed appropriate treatment for a predetermined lesion, the comparing unit 123 regards treatment corresponding to the identification result and a motion (act) of the doctor "coincide" and sends a result of the comparison to the recording unit 124 in the later stage.

On the other hand, when an identification result acquired from the identifying unit 121 relating to the medical images is "a lesion is present" and a result of the analysis acquired from the finding-motion analyzing unit 22a in the user-motion analyzing unit 122 is "treatment is absent", assuming that the doctor did not perform appropriate treatment for the predetermined lesion or assuming that treatment by the doctor was unnecessary for the lesion, the comparing unit 123 regards treatment corresponding to the identification result and a motion (act) of the doctor "do not coincide" and sends a result of the comparison to the recording unit 124 in the later stage.

Further, the comparing unit 123 may compare an identification result in the identifying unit 121 for a medical image group relating to certain constant one group among medical image groups, which are a plurality of test image groups, and a result of the analysis in the user-motion analyzing unit 122 corresponding to the medical image group relating to the certain constant one group and send a result of the comparison to the recording unit 124 in the later stage using a degree of "coincidence" or a degree of "noncoincidence" relating to the medical image group of the one group as information concerning constant weighting (for example, weighting of noncoincidence).

Subsequently, the tag imparting unit 24*a* in the recording unit 124 generates a tag corresponding to the comparison result of the comparison in the comparing unit 123 and imparts the tag to the medical images relating to the comparison result (step S15).

For example, when both results of the identification result (for example, a lesion is present) of the identification in the identifying unit 121 and the motion analysis result (for example, treatment is present or absent) of the analysis in the finding-motion analyzing unit 22*a* in the user-motion analyzing unit 122 coincide in the comparison result in the comparing unit 123 (in this case, a lesion is present and treatment is present), the tag imparting unit 24*a* generates a "coincidence tag" indicating coincidence and imparts the "coincidence tag" to the medical images relating to the comparison result.

On the other hand, when the results of the identification result acquired in the identifying unit 121 and the motion analysis result acquired in the finding-motion analyzing unit 22*a* in the user-motion analyzing unit 122 do not coincide, the tag imparting unit 24*a* generates a "noncoincidence tag" indicating noncoincidence and imparts the "noncoincidence tag" to the medical images relating to the comparison result.

Note that, without being limited to the generation and the imparting of the "coincidence tag" or the "noncoincidence tag" explained above, the tag imparting unit 24*a* may generate, based on, for example, the comparison result acquired in the comparing unit 123, a "weighting tag" indicating weight of a noncoincidence degree of the identification result acquired in the identifying unit 121 and the motion analysis result acquired in the finding-motion analyzing unit 22*a* and impart the "weighting tag" to the medical images relating to the comparison result.

Subsequently, the ranking unit 24*b* performs, according to the tag generated in the tag imparting unit 24*a*, for example, according to types of the "coincidence tag" and the "noncoincidence tag", predetermined ranking for the medical images corresponding to the tag (for example, as explained above, ranks the medical images imparted with the "coincidence tag" to the "rank 1" and ranks the medical images imparted with the "noncoincidence tag" to the "rank 2") and stores the medical images in the predetermined memory unit together with the ranking information (see FIG. 2).

Effect of First Embodiment

As explained above, with the image recording apparatus in the first embodiment, there is an effect that it is possible to record a target, identification of which an identifier is not good at, in an easily extractable data format.

Second Embodiment

Subsequently, a second embodiment of the present invention is explained.

An image recording apparatus in the second embodiment is characterized in that an analysis target of a doctor motion in a user-motion analyzing unit is different compared with the first embodiment. Since the other components are the same as the components in the first embodiment, only the difference from the first embodiment is explained. Explanation of common portions is omitted.

Figure 5:
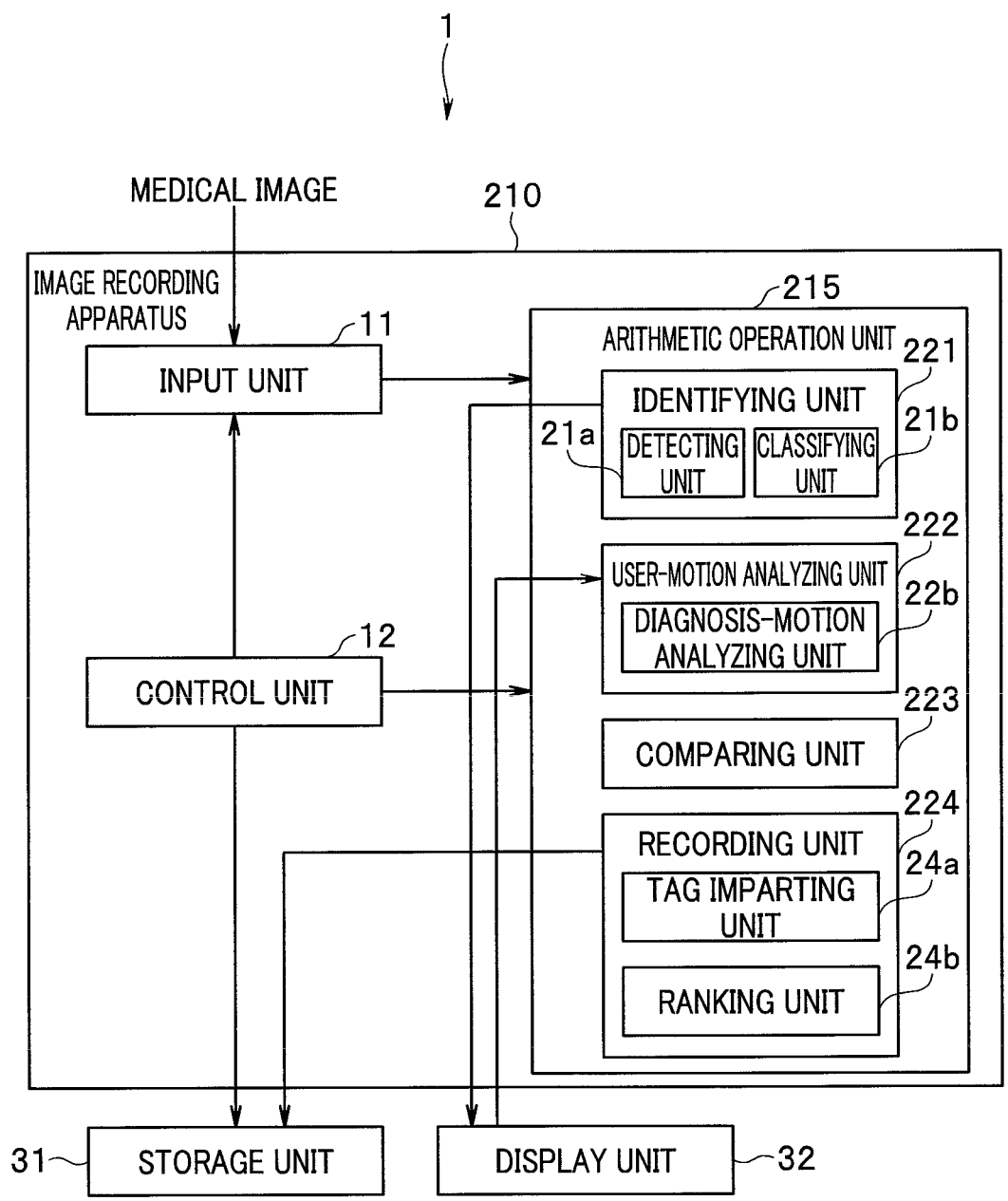
FIG. 5 is a block diagram showing a configuration of a medical system including an image recording apparatus according to a second embodiment of the present invention.
Figure 6:
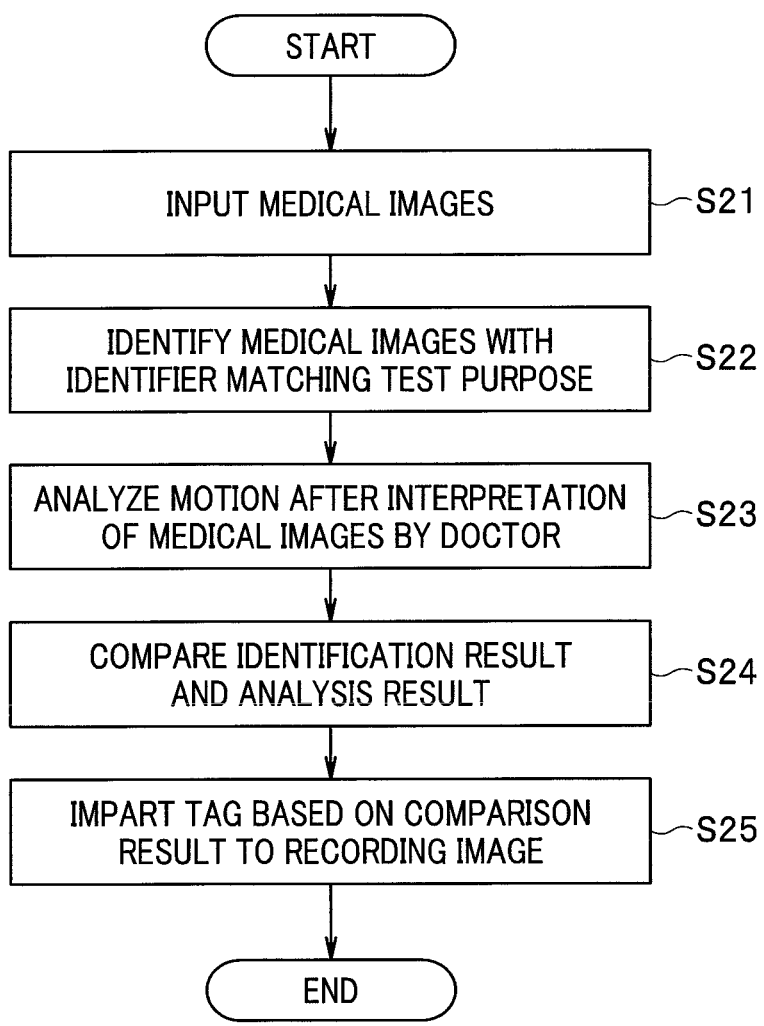
FIG. 6 is a flowchart showing action of the image recording apparatus in the second embodiment.

FIG. 5 is a block diagram showing a configuration of a medical system including the image recording apparatus according to the second embodiment of the present invention. FIG. 6 is a flowchart showing action of the image recording apparatus in the second embodiment.

As shown in FIG. 5, the medical system 1 including an image recording apparatus 210 in the second embodiment mainly includes, as in the first embodiment explained above, the image recording apparatus 210 configured to acquire a medical image and apply predetermined image processing to the medical image, the storage unit 31 connected to the image recording apparatus 210 and configured to store predetermined data, and the display unit 32 configured to display the medical image to which the image processing is applied in the image recording apparatus 210.

The image recording apparatus 210 in the second embodiment mainly includes, as in the first embodiment, the input unit 11 configured to acquire a medical image picked up in an image pickup unit in an endoscope, the control unit 12 configured to control an operation of the entire image recording apparatus 210, and an arithmetic operation unit 215 configured to execute various kinds of processing explained below on the medical image acquired in the input unit 11.

In the second embodiment, the arithmetic operation unit 215 includes an identifying unit 221, a user-motion analyzing unit 222, a comparing unit 223, and a recording unit 224. The arithmetic operation unit 215 is explained in detail below.

Note that, in the second embodiment as well, the respective units of the image recording apparatus 210 such as the arithmetic operation unit 215 and the control unit 12 may be configured as electronic circuits or may be configured as circuit blocks in an integrated circuit such as an FPGA (field programmable gate array). For example, the units may include one or more processors (CPUs or the like).

Arithmetic Operation Unit 215 in Second Embodiment

Subsequently, a detailed configuration of the arithmetic operation unit 215 in the second embodiment is explained.

The arithmetic operation unit 215 includes the identifying unit 221 configured to identify a medical image such as an endoscopic image acquired in the input unit 11 and acquire an identification result, the user-motion analyzing unit 222 configured to analyze a motion relating to interpretation of the medical image by a doctor (user) to acquire a motion analysis result, the comparing unit 223 configured to compare the identification result acquired in the identifying unit 221 and the motion analysis result acquired in the user-motion analyzing unit 222 and acquire a result of the comparison, and the recording unit 224 configured to store the medical image and information relating to the comparison result acquired in the comparing unit 223.

The identifying unit 221 has the same configuration and the same action and effects as the configuration and the action and effects of the identifying unit 121 in the first embodiment. Therefore, explanation of the identifying unit 221 is omitted. However, the identifying unit 221 identifies, based on a detection result in the detecting unit 21a or based on a classification result in the classifying unit 21b, a medical image such as an endoscopic image acquired in the input unit 11 to match a test purpose and sends a predetermined medical image to the comparing unit 223 as an identification result.

In the first embodiment explained above, the user-motion analyzing unit 122 includes the finding-motion analyzing unit 22a configured to analyze a motion relating to finding of a lesion by the doctor. In contrast, the user-motion analyzing unit 222 in the second embodiment includes a diagnosis-motion analyzing unit 22b configured to analyze a motion relating to lesion diagnosis by the doctor, who is the user.

After the doctor recognizes the identification result by the identifying unit 221, the diagnosis-motion analyzing unit 22b analyzes a motion relating to interpretation of the medical image by the doctor and acquires a motion analysis result.

More specifically, for example, after the doctor recognizes the identification result by the identifying unit 221, the diagnosis-motion analyzing unit 22b sends information relating to a diagnosis time required for diagnosis of the lesion by the doctor to the comparing unit 223 in a later stage (see FIG. 2) as a result of the analysis. The comparing unit 223 compares length of the diagnosis time with a predetermined reference value, determines, for example, whether the doctor had hesitation in diagnosis, and sends a result of the determination to a later stage.

The diagnosis-motion analyzing unit 22b sends information relating to the diagnosis inputted by the doctor to the comparing unit 223 in the later stage as a result of the analysis (see FIG. 2). The comparing unit 223 compares the identification result and the analysis result of the diagnosis, determines whether the lesion is a target for which diagnosis by the doctor is difficult and sends a result of the determination to a later stage.

Further, the diagnosis-motion analyzing unit 22b receives the input of the diagnosis by the doctor with an indicator different from an identification indicator by the identifying unit and sends information relating to the diagnosis to the comparing unit 223 in the later stage as a result of the analysis (see FIG. 2). The comparing unit 223 compares the identification result and the diagnosis information inputted with the indicator different from the identification result, determines whether the lesion is a target for which diagnosis by the doctor is difficult, and sends a result of the determination to a later stage.

"Diagnosis by a different indicator" is diagnosis carried out in every phase of diagnosis in clinical diagnosis. Examples of the "diagnosis by a different indicator" include non-expanded diagnosis, expanded diagnosis, and dyeing diagnosis.

Further, the diagnosis-motion analyzing unit 22b analyzes, about pathological information inputted after a test, information relating to a diagnosis result adjusted to an indicator identified by the identifying unit and sends a result of the analysis to the comparing unit 223 in the later stage (see FIG. 2). The comparing unit 223 compares an identification result by the identifying unit and a diagnosis result by pathology, determines whether the lesion is a target for which diagnosis by the doctor is difficult, and sends a result of the determination to the later stage.

Further, the diagnosis-motion analyzing unit 22b analyzes a treatment action by the doctor relating to diagnosis of the lesion by the doctor and sends information indicating whether predetermined treatment is performed (treatment is present or treatment is absent) to the comparing unit 223 in the later stage as a result of the analysis (see FIG. 2).

In the second embodiment, configurations and action and effects relating to the comparing unit 223 and the recording unit 224 are respectively the same as the configurations and the action and effects of the comparing unit 123 and the recording unit 124 in the first embodiment. Therefore, detailed explanation of the configurations and the action and effects is omitted.

Action of Second Embodiment

Subsequently, action of the image recording apparatus in the second embodiment is explained with reference to the explanatory diagram of FIG. 2 and using a flowchart of FIG. 6. FIG. 6 is a flowchart showing the action of the image recording apparatus in the second embodiment.

As shown in FIG. 6, in the image recording apparatus in the second embodiment, as in the first embodiment, first, the input unit 11 acquires predetermined medical images such as endoscopic images (step S21). In the present embodiment as well, the medical images are assumed to be images (endoscopic images) acquired using predetermined medical equipment (in the present embodiment, a medical endoscope apparatus) by the doctor 100 (see FIG. 2), who is the user, himself or herself according to an order (medical care policy or the like) of the doctor 100.

Subsequently, the identifying unit 221 in the image recording apparatus identifies the medical images such as the endoscopic images acquired in the input unit 11 to match a test purpose and sends the predetermined medical images to the comparing unit 223 as an identification result (step S22).

The diagnosis-motion analyzing unit 22b in the user-motion analyzing unit 222 analyzes a motion after interpretation of the medical images by the doctor 100 (see FIG. 2) and sends a result of the analysis to the comparing unit 223 (step S23).

Subsequently, the comparing unit 223 in the image recording apparatus acquires the identification result (for example, data of medical images in which a lesion is determined as present (lesion is present)) of the identification in the identifying unit 221 (see FIG. 2), acquires the motion analysis result (for example, data of medical images indicating that the doctor performed predetermined treatment after interpretation of the medical images and data of medical images indicating that the doctor did not perform the predetermined treatment) (see FIG. 2), compares the identification result and the motion analysis result, and sends a result of the comparison to the tag imparting unit 24a in the recording unit 224 (step S24).

More specifically, when an identification result acquired from the identifying unit 221 relating to the medical images is "a lesion is present" and a result of the analysis acquired from the diagnosis-motion analyzing unit 22b in the user-motion analyzing unit 222 is "treatment is present", assuming that the doctor performed appropriate treatment on a predetermined lesion, the comparing unit 223 regards that treatment corresponding to the identification result and a motion (act) of the doctor "coincide", and sends a result of the comparison to the recording unit 224 in a later stage.

On the other hand, when an identification result acquired from the identifying unit 221 relating to the medical images is "a lesion is present" and a result of the analysis acquired from the diagnosis-motion analyzing unit 22b in the user-motion analyzing unit 222 is "treatment is absent", assuming that the doctor did not perform appropriate treatment on the predetermined lesion, the comparing unit 223 regards that treatment corresponding to the identification result and a motion (act) of the doctor "do not coincide", and sends a result of the comparison to the recording unit 224 in the later stage.

Subsequently, the tag imparting unit 24a in the recording unit 224 generates a tag corresponding to the comparison result of the comparison in the comparing unit 223 and imparts the tag to the medical images relating to the comparison result (step S25).

Action of the tag imparting unit 24a and the ranking unit 24b in the recording unit 224 is the same as the action in the first embodiment. Therefore, detailed explanation of the action is omitted.

Effect of Second Embodiment

As explained above, in the image recording apparatus in the second embodiment, as in the first embodiment, there is an effect that it is possible to record a target, identification of which an identifier is not good at, in an easily extractable data format.

Third Embodiment

Subsequently, a third embodiment of the present invention is explained.

In the image recording apparatuses in the first and second embodiments, the recording unit 124 (224) includes the tag imparting unit 24a and the ranking unit 24b and ranks and records a medical image based on tag information generated in the tag imparting unit 24a.

In contrast, in an image recording apparatus in the third embodiment, a recording unit changes image quality of a medical image according to the tag information explained above, adjusts an image data amount, and records the medical image. Since the other components are the same as the components in the second embodiment, only a difference from the first and second embodiments is explained. Explanation of common portions is omitted.

Figure 7:
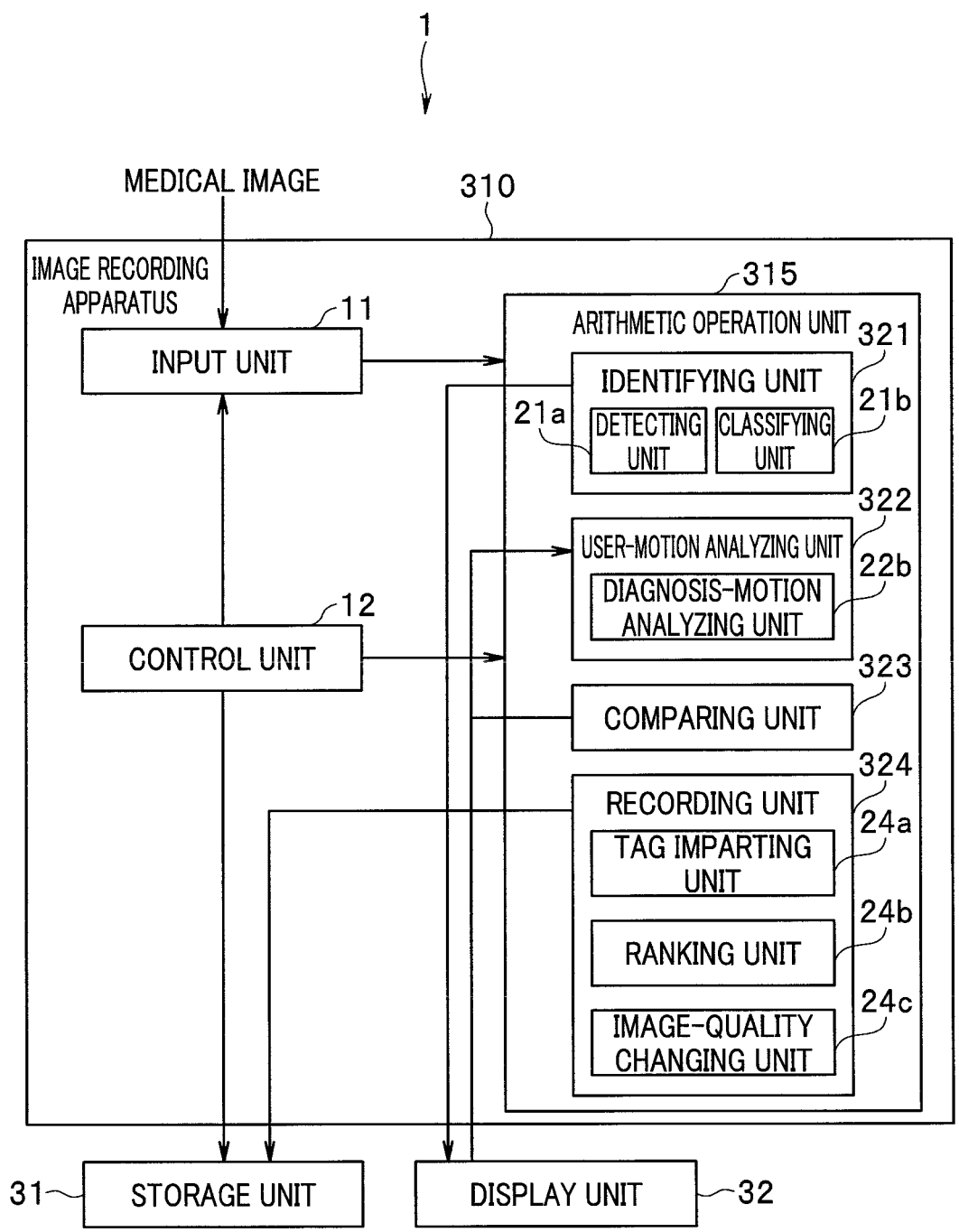
FIG. 7 is a block diagram showing a configuration of a medical system including an image recording apparatus according to a third embodiment of the present invention.
Figure 8:
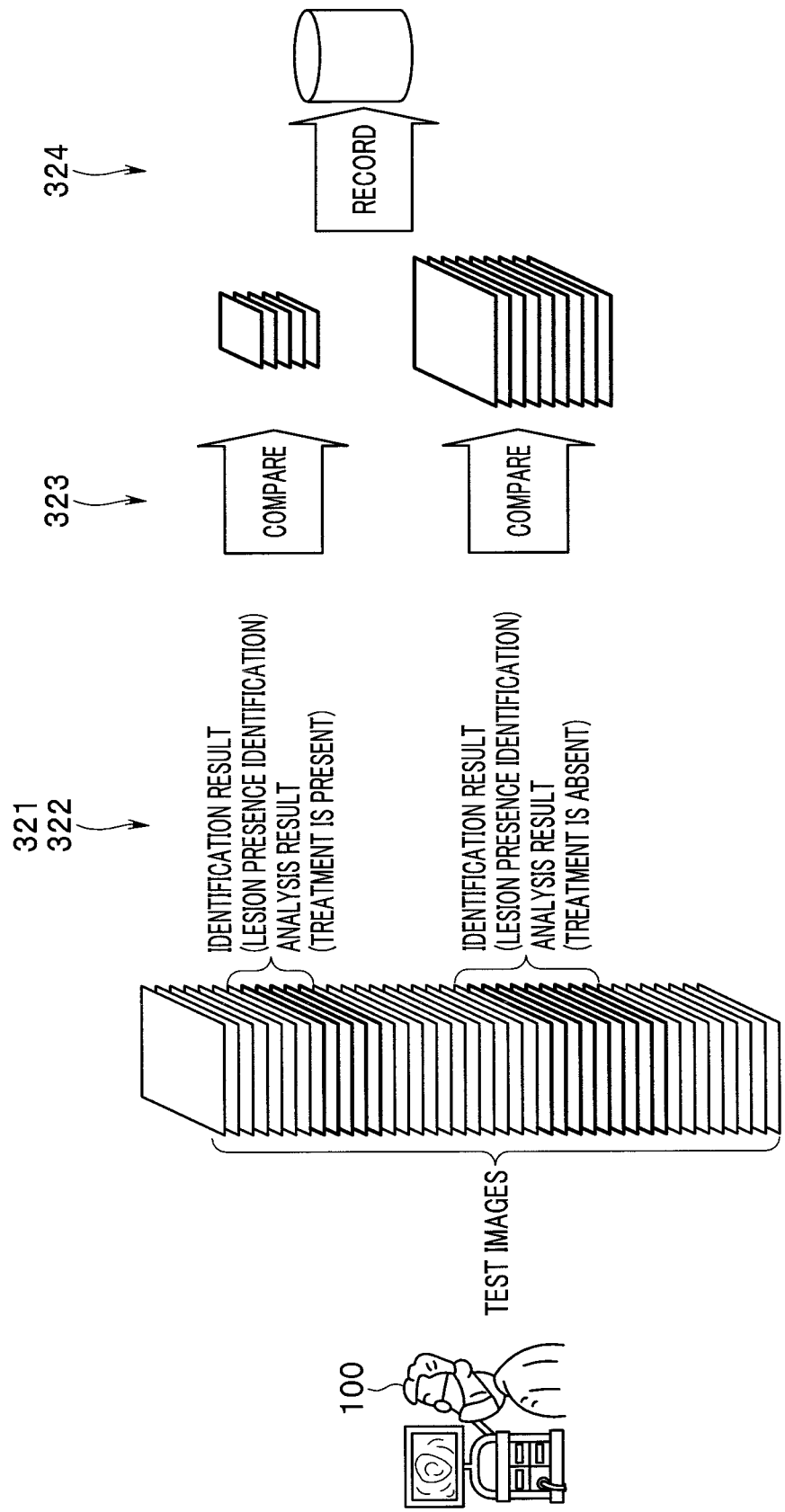
FIG. 8 is an explanatory diagram for explaining an overview of action of the image recording apparatus in the third embodiment.
Figure 9:
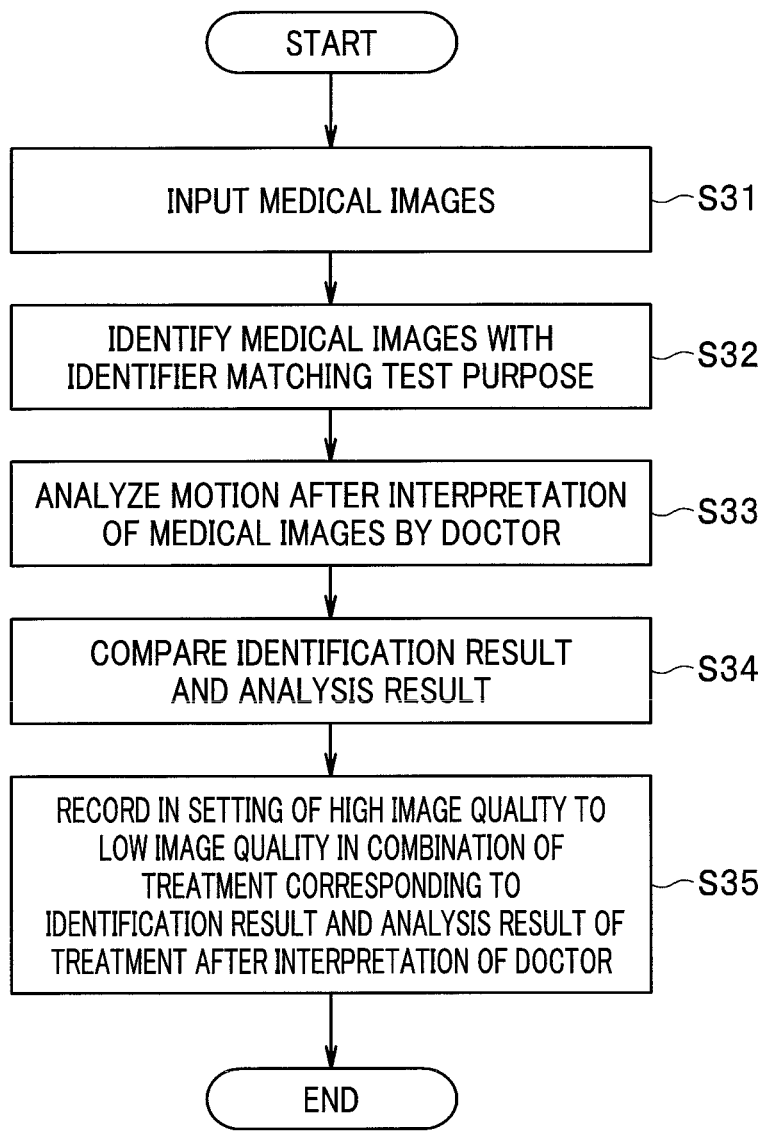
FIG. 9 is a flowchart showing action of the image recording apparatus in the third embodiment.

FIG. 7 is a block diagram showing a configuration of a medical system including the image recording apparatus according to the third embodiment of the present invention. FIG. 8 is an explanatory diagram for explaining an overview of action of the image recording apparatus in the third embodiment. FIG. 9 is a flowchart showing action of the image recording apparatus in the third embodiment.

As shown in FIG. 7, the medical system 1 including an image recording apparatus 310 in the third embodiment mainly includes, as in the first embodiment explained above, the image recording apparatus 310 configured to acquire a medical image and applies predetermined image processing to the medical image, the storage unit 31 connected to the image recording apparatus 310 and configured to store predetermined data, and a display unit 32 configured to display the medical image to which the image processing is applied in the image recording apparatus 310.

The image recording apparatus 310 in the third embodiment mainly includes, as in the first and second embodiments, the input unit 11 configured to acquire a medical image picked up in an image pickup unit in an endoscope, the control unit 12 configured to control an operation of the entire image recording apparatus 310, and an arithmetic operation unit 315 configured to execute various kinds of processing explained below on the medical image acquired in the input unit 11.

In the third embodiment, the arithmetic operation unit 315 includes an identifying unit 321, a user-motion analyzing unit 322, a comparing unit 323, and a recording unit 324. The arithmetic operation unit 315 is explained in detail below.

Note that, in the third embodiment as well, the respective units of the image recording apparatus 310 such as the arithmetic operation unit 315 and the control unit 12 may be configured as electronic circuits or may be configured as circuit blocks in an integrated circuit such as an FPGA (field programmable gate array). For example, the units may include one or more processors (CPUs or the like).

Arithmetic Operation Unit 315 in Third Embodiment

Subsequently, a detailed configuration of the arithmetic operation unit 315 in the third embodiment is explained.

The arithmetic operation unit 315 includes the identifying unit 321 configured to identify a medical image such as an endoscopic image acquired in the input unit 11 and acquire an identification result, the user-motion analyzing unit 322 configured to analyze a motion relating to interpretation of the medical image by a doctor (user) to acquire a motion analysis result, the comparing unit 323 configured to compare the identification result acquired in the identifying unit 321 and the motion analysis result acquired in the user-motion analyzing unit 322 and acquire a result of the comparison, and the recording unit 324 configured to store the medical image and information relating to the comparison result acquired in the comparing unit 323.

The identifying unit 321 has the same configuration and the same action and effects as the configuration and the action and effects of the identifying unit 221 in the second embodiment. Therefore, explanation of the identifying unit 321 is omitted. However, the identifying unit 321 identifies, based on a detection result in the detecting unit 21a or based on a classification result in the classifying unit 21b, a medical image such as an endoscopic image acquired in the input unit 11 to match a test purpose and sends a predetermined medical image to the comparing unit 323 as an identification result.

As in the second embodiment, the user-motion analyzing unit 322 includes the diagnosis-motion analyzing unit 22b configured to analyze a motion relating to lesion diagnosis by the doctor, who is the user. A configuration and action and effects of the diagnosis-motion analyzing unit 22b are the same as the configuration and the action and effects in the second embodiment. Therefore, explanation of the configuration and the action and effects is omitted.

In the third embodiment, a configuration and action and effects relating to the comparing unit 323 are the same as the configuration and the action and effects of the comparing unit 223 in the second embodiment. Therefore, detailed explanation of the configuration and the action and effects is omitted.

In the third embodiment, as in the first and second embodiments, the recording unit 324 includes a memory unit configured by a memory such as an updatable and recordable flash memory. However, the recording unit 324 includes an image-quality changing unit 24c in addition to the tag imparting unit 24a and the ranking unit 24b. Note that all of the tag imparting unit 24a, the ranking unit 24b, and the image-quality changing unit 24c are configured as circuit blocks in an integrated circuit such as an FPGA (field programmable gate army).

In the third embodiment, as in the first and second embodiments, the tag imparting unit 24a generates a tag corresponding to the comparison result acquired in the comparing unit 323 and imparts the tag to a medical image relating to the comparison result. The ranking unit 24b performs, according to the tag generated in the tag imparting unit 24a, ranking corresponding to a predetermined standard on the medical image corresponding to the tag. Note that the recording unit 324 stores, in the predetermined memory unit explained above, the medical image to which the tag is imparted by the tag imparting unit 24a.

In other words, in the third embodiment as well, the various tags explained above are generated by the tag imparting unit 24a. The respective medical images ranked according to the predetermined standard in the ranking unit 24b according to the generated tag are stored in the predetermined memory unit together with the tag information (for example, the ranking information explained above).

In the third embodiment, the image-quality changing unit 24c changes image quality relating to a medical image according to the tag generated in the tag imparting unit 24a. More specifically, when the tag generated in the tag imparting unit 24a is, for example, the "coincidence tag" or the "noncoincidence tag" explained above, the image-quality changing unit 24c adjusts the image quality according to the "coincidence tag" or the "noncoincidence tag".

For example, when an identification result acquired from the identifying unit 321 relating to a certain medical image is "a lesion is present" and a result of the analysis acquired from the user-motion analyzing unit 322 is "treatment is present", assuming that the doctor performed appropriate treatment, the comparing unit 323 regards treatment corresponding to the identification result and a motion (act) of the doctor "coincide". In response to this, the tag imparting unit 24a generates the "coincidence tag" explained above and imparts the "coincidence tag" to the medical image corresponding to the tag.

At this time, the image-quality changing unit 24c changes image quality of the medical image imparted with the "coincidence tag" and, more specifically, changes the image quality of the medical image to be low image quality. The recording unit 324 stores, in the predetermined memory unit, the medical image changed to the low image quality by the image-quality changing unit 24c and having a reduced recording capacity and a reduced transmission amount.

On the other hand, when an identification result acquired from the identifying unit 321 relating to the medical images is "a lesion is present" and a result of the analysis acquired from the user-motion analyzing unit 322 is "treatment is absent", assuming that the doctor did not perform appropriate treatment, the comparing unit 323 regards treatment corresponding to the identification result and a motion (act) of the doctor "do not coincide". In response to this, the tag imparting unit 24a generates the "noncoincidence tag" explained above and imparts the "noncoincidence tag" to the medical image corresponding to the tag.

In this case, the image-quality changing unit 24c does not change image quality for the medical image imparted with the "noncoincidence tag" and, more specifically, maintains the medical image at high image quality. The recording unit 324 stores, in the predetermined memory unit, the medical image maintained at the high image quality.

Note that, in the example explained above, according to the "coincidence tag" and the "noncoincidence tag" generated by the tag imparting unit 24a, in particular, when a generated tag is the "coincidence tag", it is possible to change an original medical image having high image quality to an image having low image quality and achieve a reduction in a recording capacity and a transmission amount relating to the medical image. However, changing conditions for image quality are not limited to this.

For example, a function of setting a medical image to a RAW image when a constant condition is satisfied may be given to the image-quality changing unit 24c. Only a medical image (coincidence tag or the like) corresponding to a predetermined tag may be set to the RAW image and recorded.

In other words, for example, in a case of a medical image that should be paid attention (image in which a characteristic lesion appears) but is advantageously recorded as a particularly precise image for which, for example, the doctor did not perform adequate treatment, it is sometimes requested to record the medical image at high image quality even if a demerit of an increase in a data capacity is sometimes considered. In this case, the medical image may be recorded as the RAW image having high image quality and other medical images may be greatly reduced in image quality to reduce a recording capacity and set to achieve a reduction in a recording capacity in total.

In addition to the adjustment of the image quality, a screen size may be adjusted based on tag information to be set to achieve a reduction in the recording capacity.

Further, based on the tag information, image processing may be applied to a medical image corresponding to the tag information as appropriate according to preset parameters to be set to achieve a reduction in the recording capacity.

In this way, in the third embodiment, the tag imparting unit 24a generates the tag information of the type explained above based on comparison information of treatment corresponding to an identification result and a result of the analysis of treatment after interpretation of the doctor and the tag is imparted to the medical image. The image-quality changing unit 24c changes, according to the tag information, image quality to be low image quality for a medical image not always required to have high image quality and achieves a reduction in a recording capacity and a transmission amount (see FIG. 8).

Note that, in the third embodiment, the image-quality changing unit 24c changes, according to tag information generated in the tag imparting unit 24a, image quality of a medical image corresponding to the tag information. However, not only this, but, for example, according to a rank of a medical image ranked in the ranking unit 24b, the image-quality changing unit 24c may change image quality relating to the medical image corresponding to the rank.

Action of Third Embodiment

Subsequently, action of the image recording apparatus in the third embodiment is explained with reference to an explanatory diagram of FIG. 8 and using a flowchart of FIG. 9. FIG. 9 is a flowchart showing action of the image recording apparatus in the third embodiment.

As shown in FIG. 9, in the image recording apparatus in the third embodiment, as in the first and second embodiments, first, the input unit 11 acquires predetermined medical images such as endoscopic images (step S31). In the present embodiment as well, the medical images are assumed to be images (endoscopic images) acquired by the doctor 100 (see FIG. 8), who is a user, himself or herself using predetermined medical equipment (in the present embodiment, a medical endoscope apparatus) according to an order (medical care policy or the like) of the doctor 100.

Subsequently, the identifying unit 321 in the image recording apparatus identifies the medical images such as the endoscopic images acquired in the input unit 11 to match a test purpose and sends the predetermined medical images to the comparing unit 323 as the identification result (step S32).

The diagnosis-motion analyzing unit 22b in the user-motion analyzing unit 322 analyzes a motion after interpretation of the medical images by the doctor 100 (see FIG. 8) and sends a result of the analysis to the comparing unit 323 (step S33).

Subsequently, the comparing unit 323 in the image recording apparatus acquires the identification result of the identification in the identifying unit 321 (see FIG. 8), acquires the motion analysis result acquired in the user-motion analyzing unit 322 (for example, data of medical images indicating that the doctor performed predetermined treatment after the interpretation of the medical images and data of medical images indicating that the doctor did not perform the treatment) (see FIG. 8), compares the identification result and the motion analysis result, and sends a result of the comparison to the tag imparting unit 24a in the recording unit 324 (step S34).

The tag imparting unit 24a generates the tag information of the type explained above based on comparison information of treatment corresponding to the identification result and a result of the analysis of the treatment after the interpretation of the doctor and imparts the tag to the medical images. The image-quality changing unit 24c changes, according to the tag information, image quality to be low image quality for medical images not always required to have high image quality and stores the medical images in the predetermined memory unit (step S35).

Effect of Third Embodiment

As explained above, with the image recording apparatus in the third embodiment, it is possible to secure an abundant information amount for an image relating to a target, identification of which an identifier is not good at, and it is possible to reduce a recording capacity of the recording unit and a transmission amount.

Fourth Embodiment

Subsequently, a fourth embodiment of the present invention is explained.

In the image recording apparatuses in the first to third embodiments, the recording unit performs ranking based on tag information generated in the tag imparting unit 24a or changes image quality and adjusts a recording capacity and a transmission amount but, in principle, records all medical images.

In contrast, in an image recording apparatus in the fourth embodiment, a recording unit secures, according to the tag information explained above, an abundant information amount for an image relating to a target, identification of which an identifier is not good at, and sets, based on comparison information of treatment corresponding to an identification result and a result of the analysis of the treatment after interpretation of a doctor, a medical image not always required to be recorded not to be stored to further reduce the recording capacity and the transmission amount.

Since the other components are the same as the components in the first and second embodiments, only a difference from the first and second embodiments is explained. Explanation of common portions is omitted.

Figure 10:
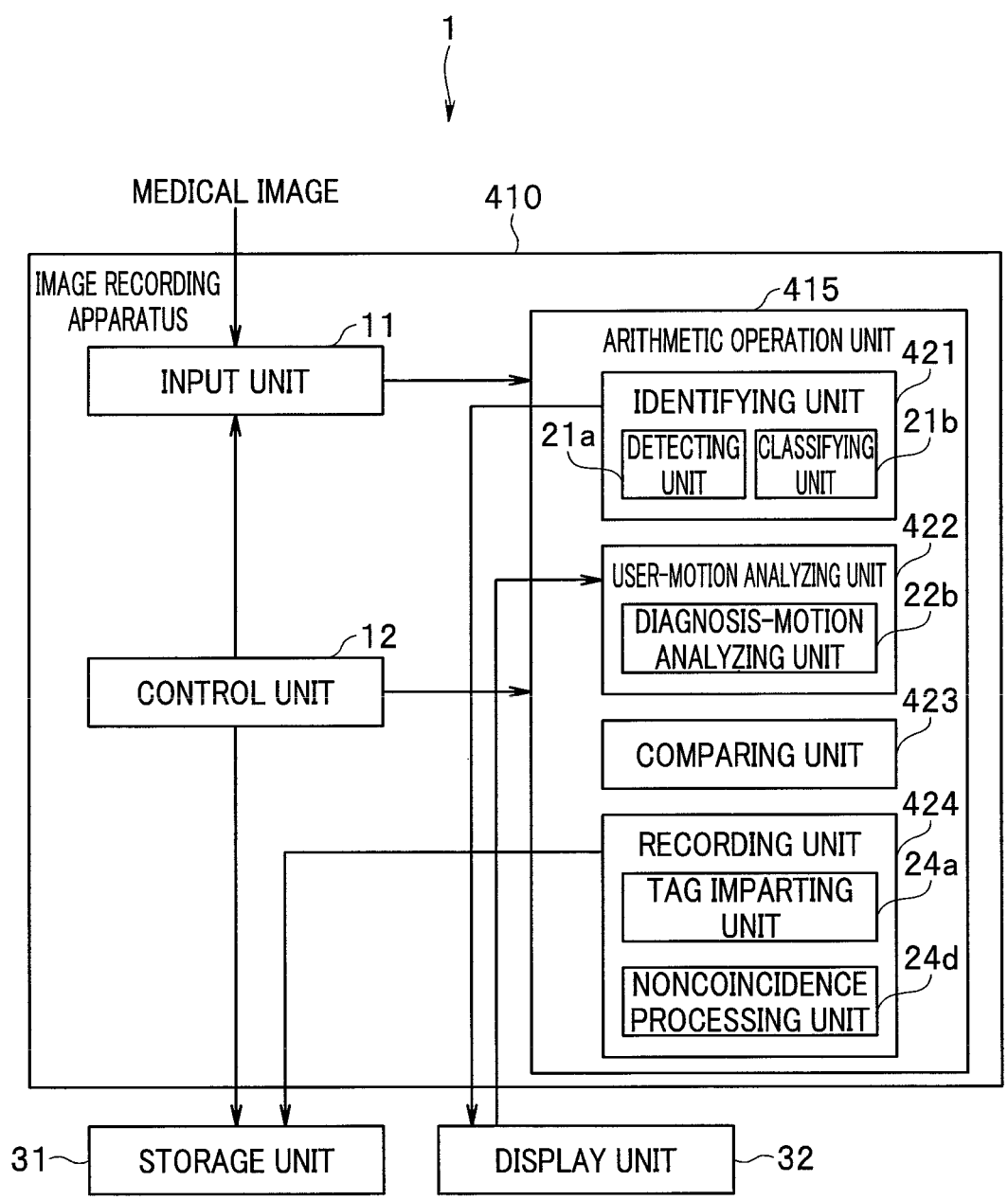
FIG. 10 is a block diagram showing a configuration of a medical system including an image recording apparatus according to a fourth embodiment of the present invention.
Figure 11:
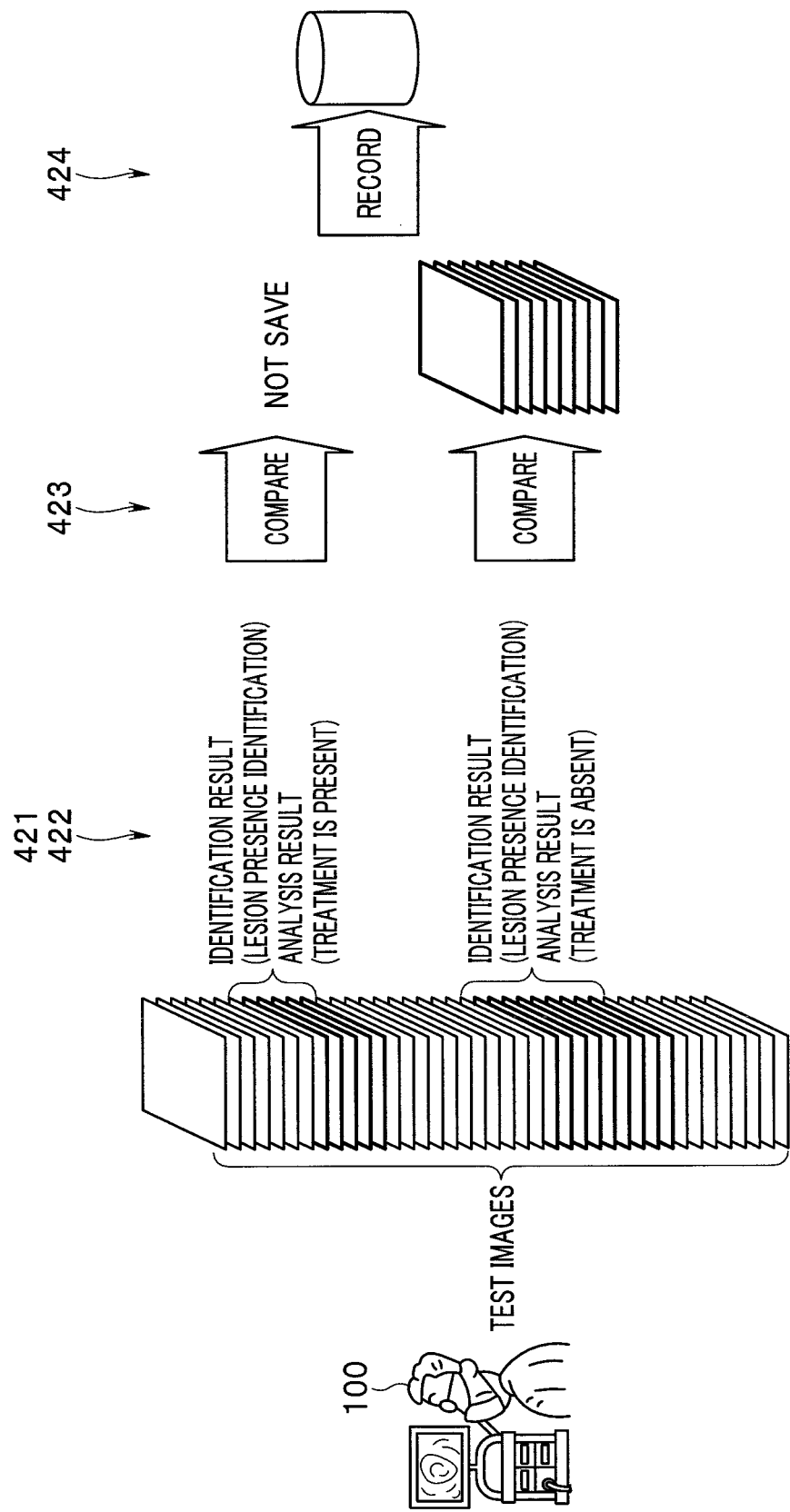
FIG. 11 is an explanatory diagram for explaining an overview of action of the image recording apparatus in the fourth embodiment.
Figure 12:
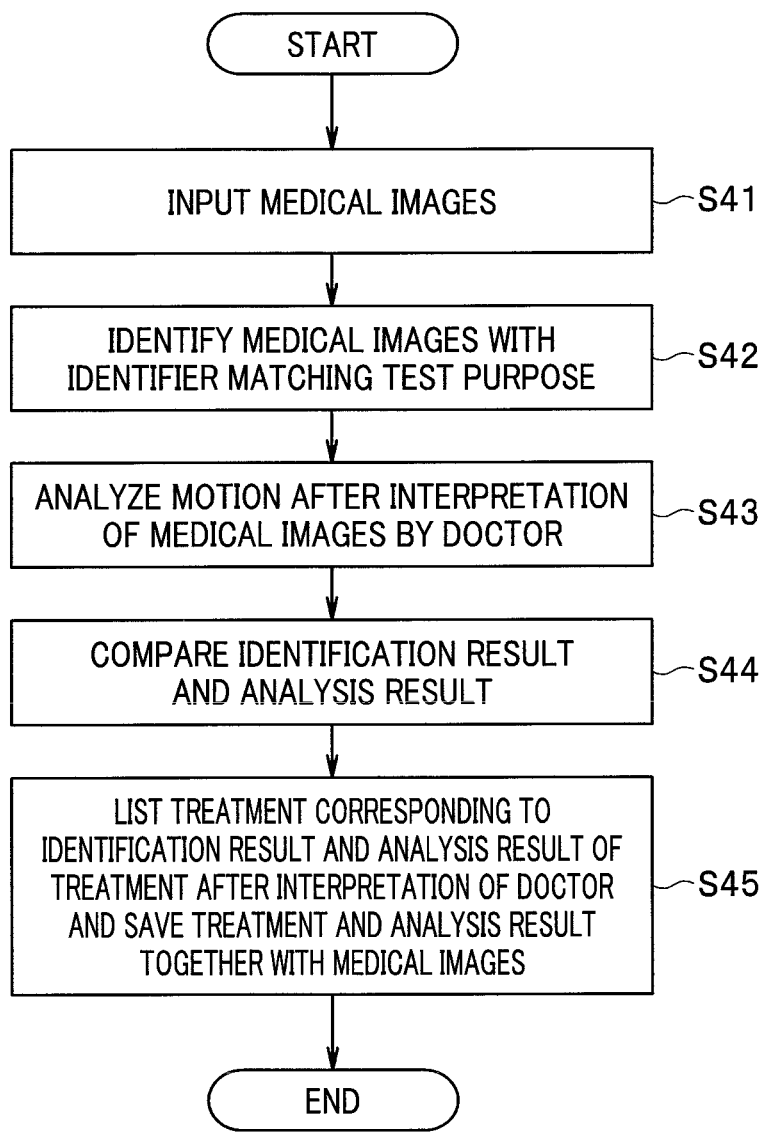
FIG. 12 is a flowchart showing action of the image recording apparatus in the fourth embodiment.

FIG. 10 is a block diagram showing a configuration of a medical system including the image recording apparatus according to the fourth embodiment of the present invention. FIG. 11 is an explanatory diagram for explaining an overview of action of the image recording apparatus in the fourth embodiment. FIG. 12 is a flowchart showing the action of the image recording apparatus in the fourth embodiment.

As shown in FIG. 10, the medical system 1 including an image recording apparatus 410 in the fourth embodiment mainly includes, as in the first embodiment explained above, the image recording apparatus 410 configured to acquire a medical image and apply predetermined image processing to the medical image, the storage unit 31 connected to the image recording apparatus 410 and configured to store predetermined data, and the display unit 32 configured to display the medical image to which the image processing is applied in the image recording apparatus 410.

The image recording apparatus 410 in the fourth embodiment mainly includes, as in the first and second embodiments, the input unit 11 configured to acquire a medical image picked up in an image pickup unit in an endoscope, the control unit 12 configured to control an operation of the entire image recording apparatus 410, and an arithmetic operation unit 415 configured to execute various kinds of processing explained below on the medical image acquired in the input unit 11.

In the fourth embodiment, the arithmetic operation unit 415 includes an identifying unit 421, a user-motion analyzing unit 422, a comparing unit 423, and a recording unit 424. The arithmetic operation unit 415 is explained in detail below.

Arithmetic Operation Unit 415 in Fourth Embodiment

Subsequently, a detailed configuration of the arithmetic operation unit 415 in the fourth embodiment is explained.

The arithmetic operation unit 415 includes the identifying unit 421 configured to identify a medical image such as an endoscopic image acquired in the input unit 11 and acquire an identification result, the user-motion analyzing unit 422 configured to analyze a motion relating to interpretation of the medical image by a doctor (user) to acquire a motion analysis result, the comparing unit 423 configured to compare the identification result acquired in the identifying unit 421 and the motion analysis result acquired in the user-motion analyzing unit 422 and acquire a result of the comparison, and the recording unit 424 configured to store the medical image and information relating to the comparison result acquired in the comparing unit 423.

The identifying unit 421 has the same configuration and the same action and effects as the configuration and the action and effects of the identifying unit 121 in the first embodiment. Therefore, explanation of the identifying unit 421 is omitted. However, the identifying unit 421 identifies, based on a detection result in the detecting unit 21a or based on a classification result in the classifying unit 21b, a medical image such as an endoscopic image acquired in the input unit 11 to match a test purpose and sends a predetermined medical image to the comparing unit 423 as an identification result.

As in the second embodiment, the user-motion analyzing unit 422 includes the diagnosis-motion analyzing unit 22b configured to analyze a motion relating to lesion diagnosis by the doctor, who is a user. A configuration and action and effects of the diagnosis-motion analyzing unit 22b are the same as the configuration and the action and effects in the second embodiment. Therefore, explanation of the configuration and the action and effects is omitted.

In the fourth embodiment, like the comparing unit 223 in the second embodiment, the comparing unit 423 compares an identification result acquired from the identifying unit 421 and a result of the analysis acquired from the user-motion analyzing unit 422 and sends information concerning whether treatment corresponding to the identification result and a motion (act) of the doctor after interpretation "coincide" or "do not coincide" to the recording unit 424 in a later stage as a result of the comparison.

In the fourth embodiment, as in the first and second embodiments, the recording unit 424 includes a memory unit configured by a memory such as an updatable and recordable flash memory. The recording unit 424 includes a noncoincidence processing unit 24d in addition to the tag imparting unit 24a. Note that both of the tag imparting unit 24a and the noncoincidence processing unit 24d are configured as circuit blocks in an integrated circuit such as an FPGA (field programmable gate array).

In the fourth embodiment, as in the first and second embodiments, the tag imparting unit 24a generates a tag corresponding to the comparison result outputted from the comparing unit 423 and imparts the tag to the medical image relating to the comparison result.

For example, when the treatment corresponding to the identification result and the motion (act) of the doctor after the interpretation "coincide", the tag imparting unit 24a generates a "coincidence tag" and imparts the "coincidence tag" to the medical image corresponding to the tag. On the other hand, when the treatment corresponding to the identification result and the motion (act) of the doctor after the interpretation "do not coincide", the tag imparting unit 24a generates a "noncoincidence tag" and imparts the "noncoincidence tag" to the medical image corresponding to the tag.

In the fourth embodiment, the noncoincidence processing unit 24d performs, according to the tag information generated in the tag imparting unit 24a, selection processing for a medical image to be stored in a memory unit. More specifically, the noncoincidence processing unit 24d performs processing not to save the medical image imparted with the "coincidence tag" and store and save only the medical image imparted with the "noncoincidence tag" in the memory unit.

In this way, in the fourth embodiment, based on comparison information of the treatment corresponding to the identification result and the result of the analysis of the treatment after the interpretation of the doctor, the tag imparting unit 24a generates the tag information of the type explained above and imparts the tag to the medical image and the noncoincidence processing unit 24d performs processing for saving only the medical image imparted with the "noncoincidence tag" in the memory unit (see FIG. 11).

Action of Fourth Embodiment

Subsequently, action of the image recording apparatus in the fourth embodiment is explained with reference to an explanatory diagram of FIG. 11 and using a flowchart of FIG. 12. FIG. 12 is a flowchart showing the action of the image recording apparatus in the fourth embodiment.

As shown in FIG. 12, in the image recording apparatus in the fourth embodiment, as in the first and second embodiments, first, the input unit 11 acquires predetermined medical images such as endoscopic images (step S41). In the present embodiment as well, the medical images are assumed to be images (endoscopic images) acquired by the doctor 100 (see FIG. 11), who is a user, himself or herself using predetermined medical equipment (in the present embodiment, a medical endoscope apparatus) according to an order (medical care policy or the like) of the doctor 100.

Subsequently, the identifying unit 421 in the image recording apparatus identifies the medical images such as the endoscopic images acquired in the input unit 11 to match a test purpose and sends the predetermined medical images to the comparing unit 423 as the identification result (step S42).

The diagnosis-motion analyzing unit 22b in the user-motion analyzing unit 422 analyzes a motion after interpretation of the medical images by the doctor 100 (see FIG. 11) and sends a result of the analysis to the comparing unit 423 (step S43).

Subsequently, the comparing unit 423 in the image recording apparatus acquires the identification result of the identification in the identifying unit 421 (see FIG. 11), acquires the motion analysis result acquired in the user-motion analyzing unit 422 (for example, data of medical images indicating that the doctor performed predetermined treatment after the interpretation of the medical images and data of medical images indicating that the doctor did not perform the treatment) (see FIG. 11), compares the identification result and the motion analysis result, and sends a result of the comparison to the tag imparting unit 24a in the recording unit 424 (step S44).

The tag imparting unit 24a generates the tag information of the type explained above based on comparison information of treatment corresponding to the identification result and a result of the analysis of the treatment after the interpretation of the doctor and imparts the tag to the medical images. According to the tag information, the noncoincidence processing unit 24d does not save, in the memory unit, medical images not required to be recorded (image imparted with the coincidence tag) and saves only medical images imparted with the "noncoincidence tag" in the memory unit (step S45).

Effect of Fourth Embodiment

As explained above, with the image recording apparatus in the fourth embodiment, it is possible to secure an abundant information amount for an image relating to a target, identification of which an identifier is not good at, and it is possible to reduce a recording capacity of the recording unit and a transmission amount.

Fifth Embodiment

Subsequently, a fifth embodiment of the present invention is explained.

In an image recording apparatus in the fifth embodiment, a recording unit lists treatment corresponding to an identification result and a result of the analysis of treatment after interpretation of a doctor and saves the treatment corresponding to the identification result and the result of the analysis together with a medical image corresponding to the treatment corresponding to the identification result and the result of the analysis. Since the other components are the same as the components in the first and second embodiments, only a difference from the first and second embodiments is explained. Explanation of common portions is omitted.

Figure 13:
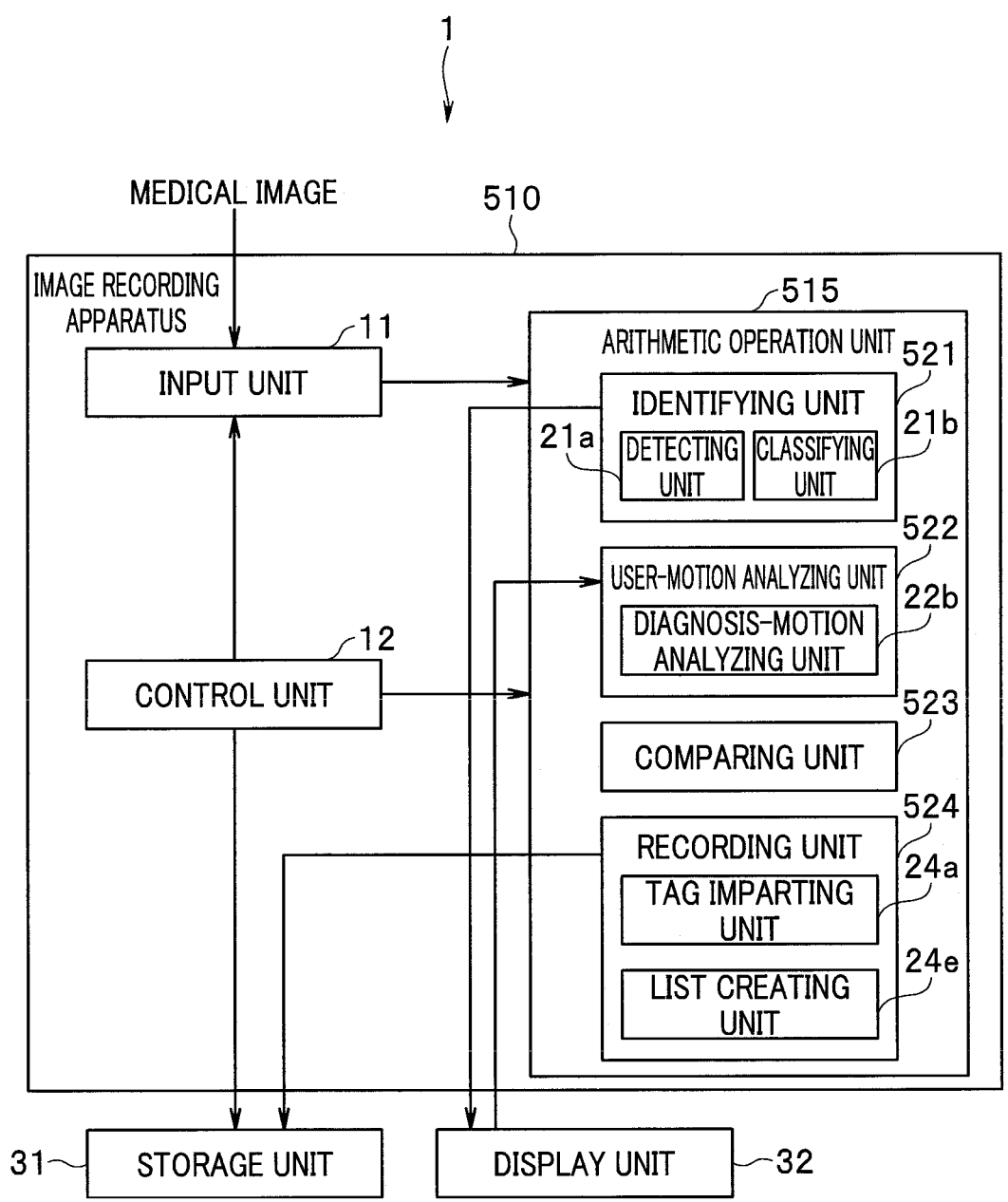
FIG. 13 is a block diagram showing a configuration of a medical system including an image recording apparatus according to a fifth embodiment of the present invention.
Figure 14:
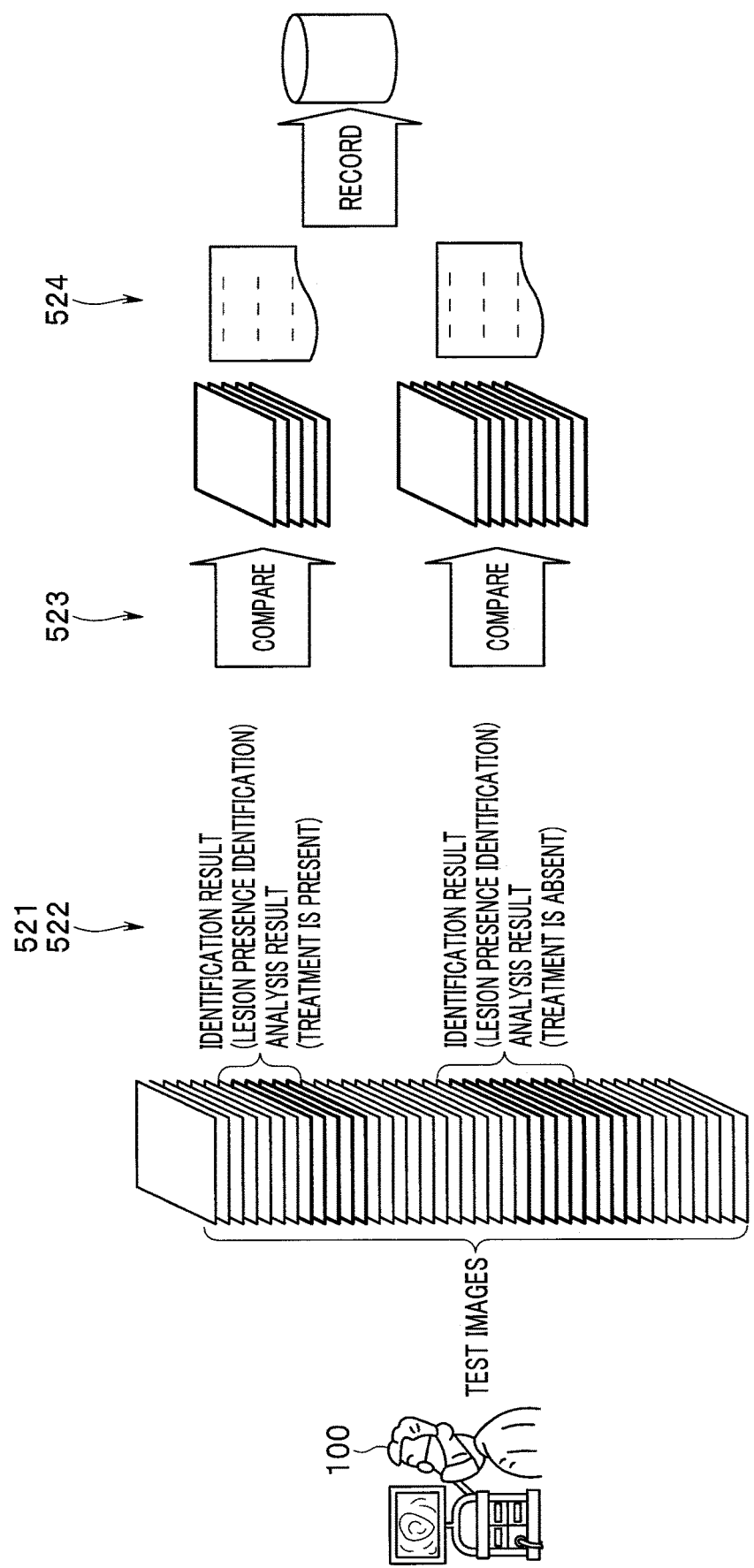
FIG. 14 is an explanatory diagram for explaining an overview of action of the image recording apparatus in the fifth embodiment.
Figure 15:
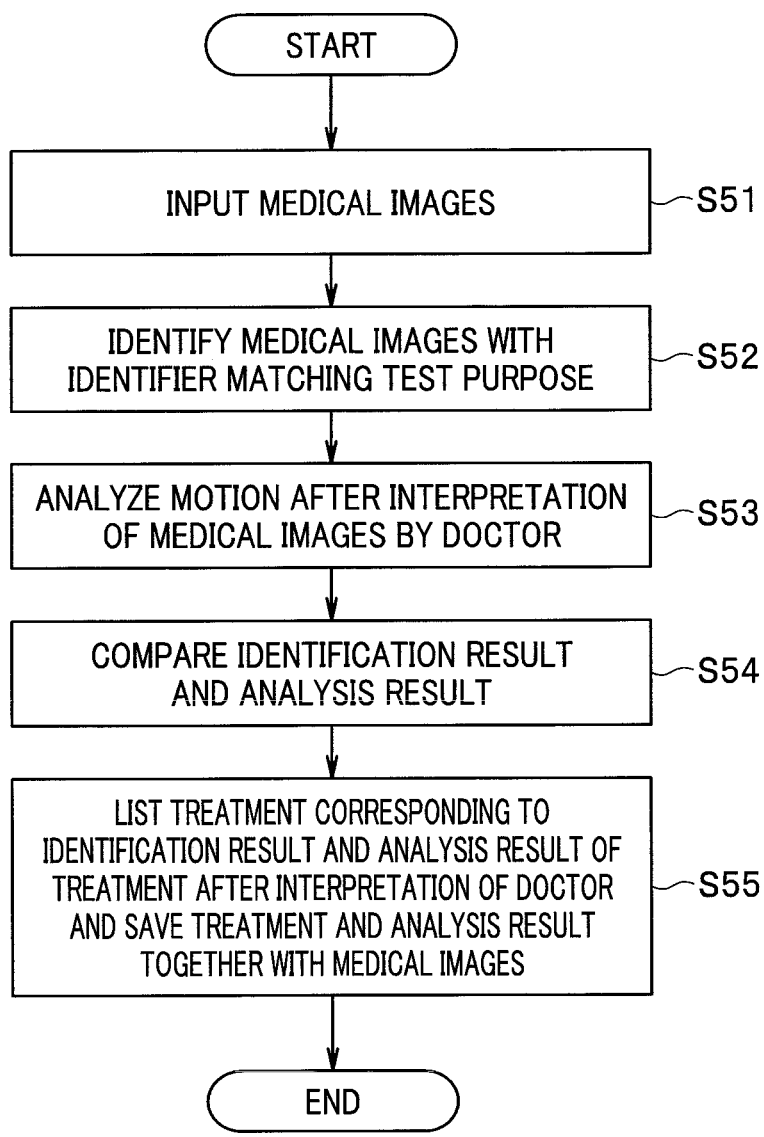
FIG. 15 is a flowchart showing action of the image recording apparatus in the fifth embodiment.

FIG. 13 is a block diagram showing a configuration of a medical system including the image recording apparatus according to the fifth embodiment of the present invention. FIG. 14 is an explanatory diagram for explaining an overview of action of the image recording apparatus in the fifth embodiment. FIG. 15 is a flowchart showing the action of the image recording apparatus in the fifth embodiment.

As shown in FIG. 13, the medical system 1 including an image recording apparatus 510 in the fifth embodiment mainly includes, as in the first embodiment explained above, the image recording apparatus 510 configured to acquire a medical image and apply predetermined image processing to the medical image, the storage unit 31 connected to the image recording apparatus 510 and configured to store predetermined data, and the display unit 32 configured to display a medical image to which image processing is applied in the image recording apparatus 510.

The image recording apparatus 510 in the fifth embodiment mainly includes, as in the first and second embodiments, the input unit 11 configured to acquire a medical image picked up in an image pickup unit in an endoscope, the control unit 12 configured to control an operation of the entire image recording apparatus 510, and an arithmetic operation unit 515 configured to execute various kinds of processing explained below on the medical image acquired in the input unit 11.

In the fifth embodiment, the arithmetic operation unit 515 includes an identifying unit 521, a user-motion analyzing unit 522, a comparing unit 523, and a recording unit 524. The arithmetic operation unit 515 is explained in detail below.

Arithmetic Operation Unit 515 in Fifth Embodiment

Subsequently, a detailed configuration of the arithmetic operation unit 515 in the fifth embodiment is explained.

The arithmetic operation unit 515 includes the identifying unit 521 configured to identify a medical image such as an endoscopic image acquired in the input unit 11 and acquire an identification result, the user-motion analyzing unit 522 configured to analyze a motion relating to interpretation of the medical image by the doctor (user) to acquire a motion analysis result, the comparing unit 523 configured to compare the identification result acquired in the identifying unit 521 and the motion analysis result acquired in the user-motion analyzing unit 522 and acquire a result of the comparison, and the recording unit 524 configured to store the medical image and information relating to the comparison result acquired in the comparing unit 523.

The identifying unit 521 has the same configuration and the same action and effects as the configuration and the action and effects of the identifying unit 121 in the first embodiment. Therefore, explanation of the identifying unit 521 is omitted. However, the identifying unit 521 identifies, based on a detection result in the detecting unit 21a or based on a classification result in the classifying unit 21b, a medical image such as an endoscopic image acquired in the input unit 11 to match a test purpose and sends a predetermined medical image to the comparing unit 523 as an identification result.

As in the second embodiment, the user-motion analyzing unit 522 includes the diagnosis-motion analyzing unit 22b configured to analyze a motion relating to lesion diagnosis by the doctor, who is the user. A configuration and action and effects of the diagnosis-motion analyzing unit 22b are the same as the configuration and the action and effects in the second embodiment. Therefore, explanation of the configuration and the action and effects is omitted.

In the fifth embodiment, like the comparing unit 223 in the second embodiment, the comparing unit 523 compares an identification result acquired from the identifying unit 521 and a result of the analysis acquired from the user-motion analyzing unit 522 and sends information concerning whether treatment corresponding to the identification result and a motion (act) of the doctor after interpretation "coincide" or "do not coincide" to the recording unit 524 in a later stage as a result of the comparison.

In the fifth embodiment, as in the first and second embodiments, the recording unit 524 includes a memory unit configured by a memory such as an updatable and recordable flash memory. The recording unit 424 includes a list creating unit 24e in addition to the tag imparting unit 24a.

In the fifth embodiment, as in the first and second embodiments, the tag imparting unit 24a generates a tag corresponding to the comparison result outputted from the comparing unit 523 and imparts the tag to the medical image relating to the comparison result.

For example, when the treatment corresponding to the identification result and the motion (act) of the doctor after the interpretation "coincide", the tag imparting unit 24a generates a "coincidence tag" and imparts the "coincidence tag" to the medical image corresponding to the tag. On the other hand, when the treatment corresponding to the identification result and the motion (act) of the doctor after the interpretation "do not coincide", the tag imparting unit 24a generates a "noncoincidence tag" and imparts the "noncoincidence tag" to the medical image corresponding to the tag.

In the fifth embodiment, the list creating unit 24e creates, according to an identification result acquired from the identifying unit 521 and a result of the analysis acquired from the user-motion analyzing unit 522, a list linked to the analysis result and saves the list together with a medical image.

In this way, in the fifth embodiment, the tag imparting unit 24a generates the predetermined tag information based on the comparison information of the treatment corresponding to the identification result and the result of the analysis of the treatment after the interpretation of the doctor and imparts the tag to the medical image. The list creating unit 24e creates and saves the list linked to the analysis result (see FIG. 14).

Action of Fifth Embodiment

Subsequently, action of the image recording apparatus in the fifth embodiment is explained with reference to an explanatory diagram of FIG. 14 and using a flowchart of FIG. 15. FIG. 15 is a flowchart showing the action of the image recording apparatus in the fifth embodiment.

As shown in FIG. 15, in the image recording apparatus in the fifth embodiment, as in the first and second embodiments, first, the input unit 11 acquires predetermined medical images such as endoscopic images (step S51). In the present embodiment as well, the medical images are assumed to be images (endoscopic images) acquired by the doctor 100 (see FIG. 14), who is a user, himself or herself using predetermined medical equipment (in the present embodiment, a medical endoscope apparatus) according to an order (medical care policy or the like) of the doctor 100.

Subsequently, the identifying unit 521 in the image recording apparatus identifies the medical images such as the endoscopic images acquired in the input unit 11 to match a test purpose and sends the predetermined medical images to the comparing unit 523 as an identification result (step S52).

The diagnosis-motion analyzing unit 22b in the user-motion analyzing unit 522 analyzes a motion after interpretation of the medical images by the doctor 100 (see FIG. 14) and sends a result of the analysis to the comparing unit 523 (step S53).

Subsequently, the comparing unit 523 in the image recording apparatus acquires the identification result of the identification in the identifying unit 521 (see FIG. 14), acquires the motion analysis result acquired in the user-motion analyzing unit 522 (for example, data of medical images indicating that the doctor performed predetermined treatment after the interpretation of the medical images and data of medical images indicating that the doctor did not perform the treatment) (see FIG. 14), compares the identification result and the motion analysis result, and sends a result of the comparison to the tag imparting unit 24a in the recording unit 524 (step S54).

The tag imparting unit 24a generates predetermined tag information based on comparison information of treatment corresponding to the identification result and a result of the analysis of the treatment after the interpretation of the doctor and imparts the tag to the medical images. The list creating unit 24e creates and saves a list linked with the analysis result (step S55).

Effect of Fifth Embodiment

As explained above, with the image recording apparatus in the fifth embodiment, there is an effect that it is possible to record a target, identification of which an identifier is not good at, in an easily extractable data format.

Sixth Embodiment

Subsequently, a sixth embodiment of the present invention is explained.

An image recording apparatus in the sixth embodiment includes a learning-target setting unit configured to set, based on a comparison result in a comparing unit, a medical image to be a target of additional learning and further includes an additional learning unit configured to execute additional learning of a learning network in an identifying unit in only a medical image to which a tag for learning target is imparted. Since the other components are the same as the components in the first embodiment, only a difference from the first embodiment is explained. Explanation of common portions is omitted.

Figure 16:
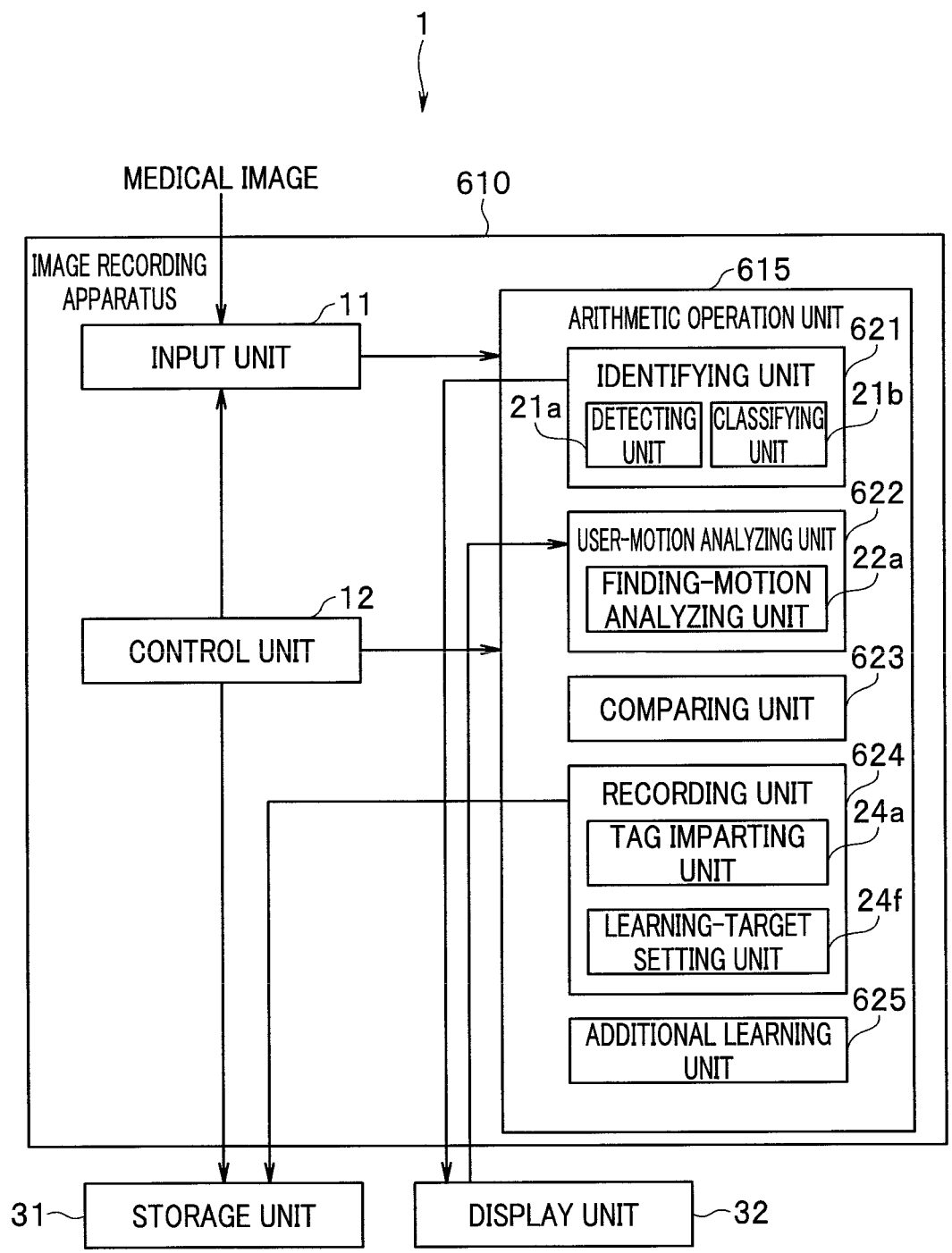
FIG. 16 is a block diagram showing a configuration of a medical system including an image recording apparatus according to a sixth embodiment of the present invention.
Figure 17:
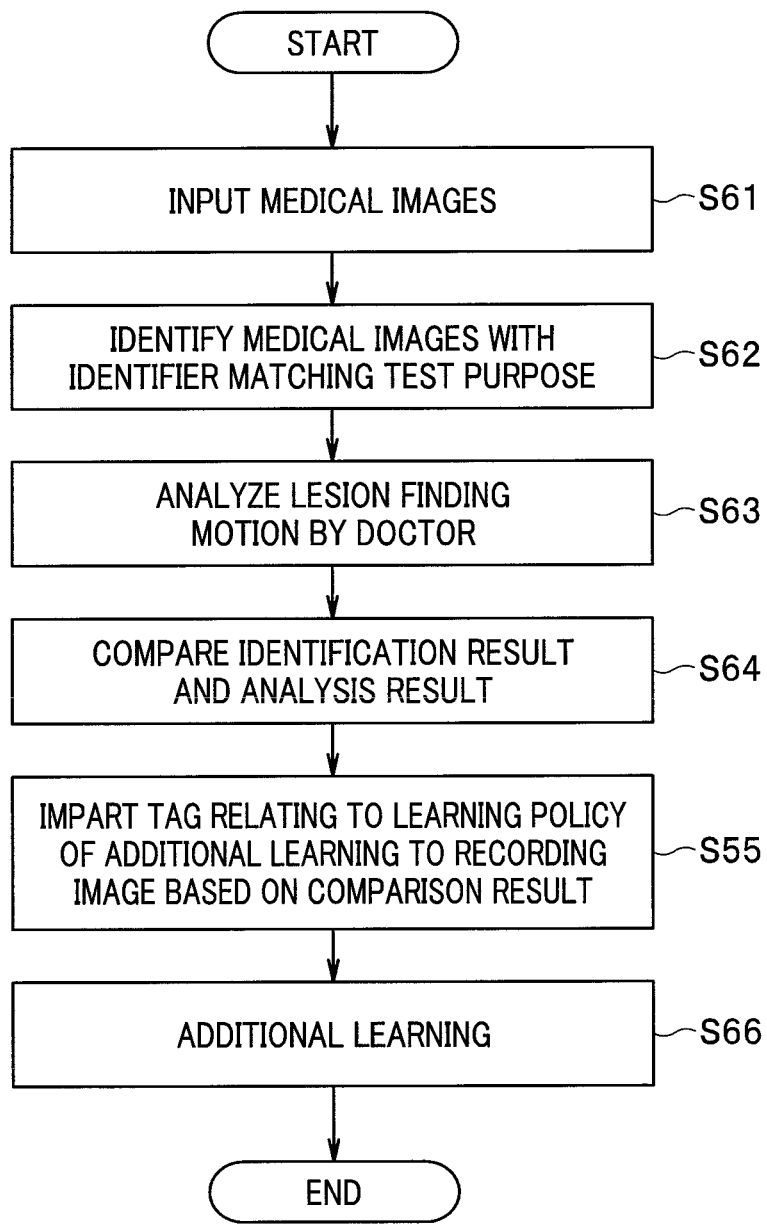
FIG. 17 is a flowchart showing action of the image recording apparatus in the sixth embodiment.

FIG. 16 is a block diagram showing a configuration of a medical system including the image recording apparatus in the sixth embodiment of the present invention. FIG. 17 is a flowchart showing action of the image recording apparatus in the sixth embodiment.

As shown in FIG. 16, the medical system 1 including an image recording apparatus 610 in the sixth embodiment mainly includes, as in the first embodiment explained above, the image recording apparatus 610 configured to acquire a medical image and apply predetermined image processing to the medical image, the storage unit 31 connected to the image recording apparatus 610 and configured to store predetermined data, and the display unit 32 configured to display the medical image to which the image processing is applied in the image recording apparatus 610.

The image recording apparatus 610 in the sixth embodiment mainly includes, as in the first embodiment, the input unit 11 configured to acquire a medical image picked up in an image pickup unit in an endoscope, the control unit 12 configured to control an operation of the entire image recording apparatus 610, and an arithmetic operation unit 615 configured to execute various kinds of processing explained below on the medical image acquired in the input unit 11.

In the sixth embodiment, the arithmetic operation unit 615 includes an identifying unit 621, a user-motion analyzing unit 622, a comparing unit 623, and a recording unit 624. The arithmetic operation unit 615 is explained in detail below.

Arithmetic Operation Unit 615 in Sixth Embodiment

Subsequently, a detailed configuration of the arithmetic operation unit 615 in the sixth embodiment is explained.

The arithmetic operation unit 615 includes the identifying unit 621 configured to identify a medical image such as an endoscopic image acquired in the input unit 11 and acquire an identification result, the user-motion analyzing unit 622 configured to analyze a motion relating to interpretation of the medical image by a doctor (user) to acquire a motion analysis result, the comparing unit 623 configured to compare the identification result acquired in the identifying unit 621 and the motion analysis result acquired in the user-motion analyzing unit 622 and acquire a result of the comparison, and the recording unit 624 configured to store the medical image and information relating to the comparison result acquired in the comparing unit 623.

The identifying unit 621 has the same configuration and the same action and effects as the configuration and the action and effects of the identifying unit 121 in the first embodiment. Therefore, explanation of the identifying unit 621 is omitted.

As in the first embodiment, the user-motion analyzing unit 622 includes the finding-motion analyzing unit 22a configured to analyze a motion relating to lesion diagnosis by the doctor, who is the user. A configuration and action and effects of the finding-motion analyzing unit 22a are the same as the configuration and the action and effects in the first embodiment. Therefore, explanation of the configuration and the action and effects is omitted.

In the sixth embodiment, like the comparing unit 123 in the first embodiment, the comparing unit 623 compares an identification result acquired from the identifying unit 621 and a result of the analysis acquired from the user-motion analyzing unit 622 and sends information concerning whether treatment corresponding to the identification result and a motion (act) of the doctor "coincide" or "do not coincide" to the recording unit 624 in a later stage as a result of the comparison.

In the sixth embodiment, as in the first embodiment, the recording unit 624 includes a memory unit configured by a memory such as an updatable and recordable flash memory. The recording unit 624 includes a learning-target setting unit 24f in addition to the tag imparting unit 24a.

In the sixth embodiment, the learning-target setting unit 24f sets, based on the comparison result acquired in the comparing unit 623, a medical image to be a target of additional learning.

In the sixth embodiment, as in the first embodiment, the tag imparting unit 24a generates a tag corresponding to the comparison result outputted from the comparing unit 623 and imparts the tag to a medical image relating to the comparison result. The tag imparting unit 24a generates a tag for learning target to be imparted to the medical image set in the learning-target setting unit 24f and imparts the tag for learning target to the medical image.

Further, the arithmetic operation unit 615 in the sixth embodiment includes an additional learning unit 625 configured to execute additional learning of a learning network in the identifying unit 621 only in the medical image to which the tag for learning target is imparted.

Action of Sixth Embodiment

Subsequently, action of the image recording apparatus in the sixth embodiment is explained using a flowchart of FIG. 17. FIG. 17 is a flowchart showing the action of the image recording apparatus in the sixth embodiment.

As shown in FIG. 17, in the image recording apparatus in the sixth embodiment, as in the first embodiment, first, the input unit 11 acquires predetermined medical images such as endoscopic images (step S61). In the present embodiment as well, the medical images are assumed to be images (endoscopic images) acquired by the doctor, who is the user, himself or herself using predetermined medical equipment (in the present embodiment, a medical endoscope apparatus) according to an order (medical care policy or the like) of the doctor.

Subsequently, the identifying unit 621 identifies the medical images such as the endoscopic images acquired in the input unit 11 to match a test purpose and sends the predetermined medical images to the comparing unit 623 as the identification result (step S62).

The finding-motion analyzing unit 22a in the user-motion analyzing unit 622 analyzes a motion of the doctor and sends a result of the analysis to the comparing unit 623 (step S63).

Subsequently, the comparing unit 623 acquires the identification result of the identification in the identifying unit 621, acquires the motion analysis result acquired in the user-motion analyzing unit 622, compares the identification result and the motion analysis result, and sends a result of the comparison to the tag imparting unit 24a in the recording unit 624 (step S64).

The learning-target setting unit 24f sets, based on the comparison result acquired in the comparing unit 623, medical images to be a target of additional learning (sets a preset tag such as a noncoincidence tag as the target of the additional learning). The tag imparting unit 24a generates a tag for learning target to be imparted to the medical images set in the learning-target setting unit 24f and imparts the tag for learning target to the medical images (step S65).

Further, the additional learning unit 625 in the arithmetic operation unit 615 executes additional learning of a learning network in the identifying unit 621 in only the medical images to which the tag for learning target is imparted by the tag imparting unit 24a (step S66).

Effect of Sixth Embodiment

As explained above, with the image recording apparatus in the sixth embodiment, in addition to the effect according to the first embodiment, since a medical image to be a target of additional learning is selected based on a comparison result of treatment corresponding to an identification result and a result of the analysis of treatment of the doctor and additional learning of a learning network in an identifying unit is executed for only the selected medical image, it is possible to more accurately perform learning.

Seventh Embodiment

Subsequently, a seventh embodiment of the present invention is explained.

An image recording apparatus in the seventh embodiment includes a transfer unit configured to transfer, to an external recording apparatus, a medical image stored in the memory unit in the recording unit in the image recording apparatus as in the first to sixth embodiments and information relating to a comparison result incidental to the medical image. Since the other components are the same as the components in the first embodiment, only a difference from the first embodiment is explained. Explanation of common portions is omitted.

Figure 18:
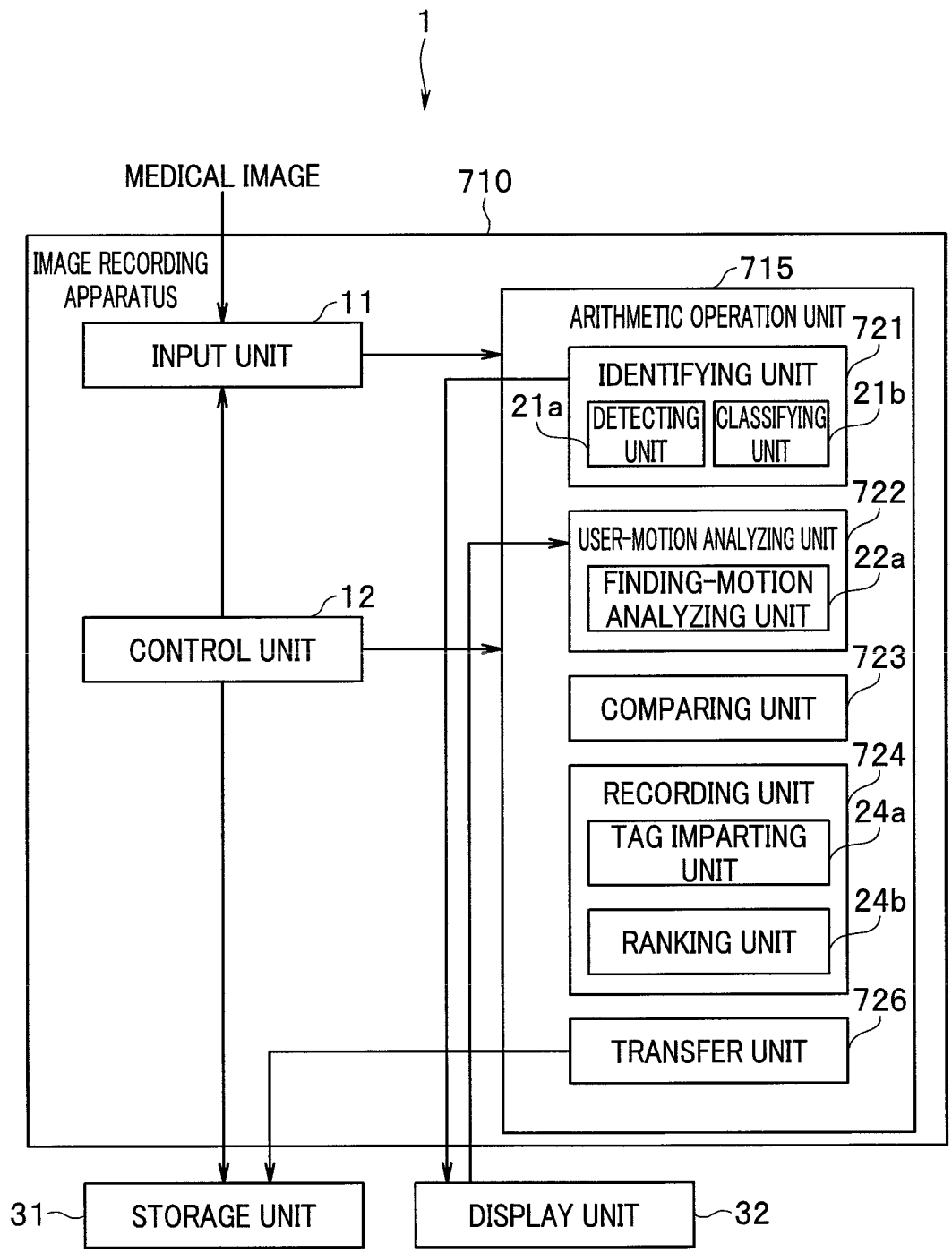
FIG. 18 is a block diagram showing a configuration of a medical system including an image recording apparatus according to a seventh embodiment of the present invention.

FIG. 18 is a block diagram showing a configuration of a medical system including the image recording apparatus according to the seventh embodiment of the present invention.

As shown in FIG. 18, the medical system 1 including an image recording apparatus 710 in the seventh embodiment mainly includes, as in the first embodiment explained above, the image recording apparatus 710 configured to acquire a medical image and apply predetermined image processing to the medical image, the storage unit 31 connected to the image recording apparatus 710 and configured to store predetermined data, and the display unit 32 configured to display the medical image to which the image processing is applied in the image recording apparatus 710.

The storage unit 31 is an external data storing unit connected to the image recording apparatus 710. In the seventh embodiment, the storage unit 31 has a function of storing a medical image and information relating to a comparison result incidental to the medical image stored in a memory unit in a recording unit 724 in the image recording apparatus 710.

Note that the storage unit 31 is realized by various memories such as an updatable and recordable flash memory, an information recording medium such as a hard disk, an SSD, or a CD-ROM, a reading apparatus for the information recording medium, or the like. Alternatively, the storage unit 31 may be a file server set in a medical base such as a hospital via a not-shown internal network (network in the hospital).

The image recording apparatus 710 in the seventh embodiment mainly includes, as in the first embodiment, the input unit 11 configured to acquire a medical image picked up in an image pickup unit in an endoscope, the control unit 12 configured to control an operation of the entire image recording apparatus 710, and an arithmetic operation unit 715 configured to execute various kinds of processing explained below on the medical image acquired in the input unit 11.

In the seventh embodiment, the arithmetic operation unit 715 includes an identifying unit 721, a user-motion analyzing unit 722, a comparing unit 723, and a recording unit 724. The arithmetic operation unit 715 is explained in detail below.

Arithmetic Operation Unit 715 in Seventh Embodiment

Subsequently, a detailed configuration of the arithmetic operation unit 715 in the seventh embodiment is explained.

The arithmetic operation unit 715 includes the identifying unit 721 configured to identify a medical image such as an endoscopic image acquired in the input unit 11 and acquire an identification result, the user-motion analyzing unit 722 configured to analyze a motion relating to interpretation of the medical image by a doctor (user) to acquire a motion analysis result, the comparing unit 723 configured to compare the identification result acquired in the identifying unit 721 and the motion analysis result acquired in the user-motion analyzing unit 722 and acquire a result of the comparison, and the recording unit 724 configured to store the medical image and information relating to the comparison result acquired in the comparing unit 723.

The identifying unit 721 has the same configuration and the same action and effects as the configuration and the action and effects of the identifying unit 121 in the first embodiment. Therefore, explanation of the identifying unit 721 is omitted.

As in the first embodiment, the user-motion analyzing unit 722 includes the finding-motion analyzing unit 22a configured to analyze a motion relating to lesion diagnosis by the doctor, who is the user. A configuration and action and effects of the finding-motion analyzing unit 22a are the same as the configuration and the action and effects in the first embodiment. Therefore, explanation of the configuration and the action and effects is omitted.

In the seventh embodiment, like the comparing unit 123 in the first embodiment, the comparing unit 723 compares an identification result acquired from the identifying unit 721 and a result of the analysis acquired from the user-motion analyzing unit 722 and sends information concerning whether treatment corresponding to the identification result and a motion (act) of the doctor "coincide" or "do not coincide" to the recording unit 724 in a later stage.

In the seventh embodiment, as in the first embodiment, the recording unit 724 includes a memory unit configured by a memory such as an updatable and recordable flash memory. The recording unit 724 includes the tag imparting unit 24a and the ranking unit 24b configured to play the same functions as the functions in the first embodiment.

In the seventh embodiment, the arithmetic operation unit 715 includes a transfer unit 726 for transferring information relating to a medical image stored in a memory unit of the recording unit 724 to an external recording apparatus, for example, the storage unit 31 explained above.

As explained above, in the memory unit of the recording unit 724, a medical image recorded in a set recording scheme, for example, a medical image selected by a tag based on a comparison result of treatment corresponding to the identification result and a motion (act) of the doctor is stored together with information incidental to the medical image. The transfer unit 726 in the seventh embodiment has a function of transferring data relating to the medical images to an external apparatus such as the storage unit 31 explained above.

Effect of Seventh Embodiment

As explained above, with the image recording apparatus in the seventh embodiment, in addition to the effect according to the first embodiment, medical image data selected by a predetermined tag based on a comparison result of treatment corresponding to an identification result and a result of the analysis of treatment of the doctor and stored can be accurately transferred to an external recording apparatus together with information incidental to the medical image data.

The present invention is not limited to the embodiments explained above. Various changes, alterations, and the like are possible within a range not changing the gist of the present invention.

What is claimed is:

1. An information processing apparatus comprising:
one or more processors comprising hardware, wherein the one or more processors are configured to:
acquire a medical image;
perform identification of whether the medical image has a predetermined region;
perform analysis of whether one or more predetermined motions is performed by a medical device that acquired the medical image;
perform comparison of a result of the identification and a result of the analysis to determine one of:
coincidence of identification of the medical image as having the predetermined region and performance of the one or more predetermined motions by the medical device that captured the medical image, and
noncoincidence of identification of the medical image as having the predetermined region and performance of the one or more predetermined motions by the medical device that captured the medical image;
generate one of a plurality of tags based on a result of the comparison; and
impart the tag to the medical image.

2. The information processing apparatus according to claim 1, wherein, in performing the identification, the one or more processors are configured to identify whether the medical image has a predetermined abnormal region as the predetermined region.

3. The information processing apparatus according to claim 1, wherein, in performing the identification, the one or more processors are configured to automatically classify the medical image based on a predetermined indicator to identify the medical image having the predetermined region.

4. The information processing apparatus according to claim 1, wherein, in performing the analysis, the one or more processors are configured to analyze whether one or more predetermined motions relating to finding a lesion is performed by the medical device that acquired the medical image.

5. The information processing apparatus according to claim 4,
wherein the medical device comprises an endoscope, and
wherein, in performing the analysis, the one or more processors are configured to determine whether one or more predetermined actions of an insertion section of the endoscope relating to finding the lesion is performed.

6. The information processing apparatus according to claim 4,
wherein the medical device comprises an endoscope, and
wherein, in performing the analysis, the one or more processors are configured to determine whether one or more predetermined actions of an endoscope operation section of the endoscope relating to finding the lesion is performed.

7. The information processing apparatus according to claim 4,
wherein the medical device comprises an endoscope, and
wherein, in performing the analysis, the one or more processors are configured to determine presence or absence of treatment by the endoscope in the one or more predetermined motions relating to finding the lesion.

8. The information processing apparatus according to claim 1, wherein, in performing the analysis, the one or more processors are configured to analyze whether one or more predetermined motions relating to a lesion diagnosis is performed by the medical device that acquired the medical image.

9. The information processing apparatus according to claim 8, wherein, in performing the analysis, the one or more processors are configured to analyze a diagnosis time of the predetermined motions relating to the lesion diagnosis performed by the medical device that acquired the medical image.

10. The information processing apparatus according to claim 8, wherein, in performing the analysis, the one or more processors are configured to analyze information relating to a diagnosis inputted by a user.

11. The information processing apparatus according to claim 8, wherein, in performing the analysis, the one or more processors are configured to analyze a diagnosis result by an indicator different from the result of the identification.

12. The information processing apparatus according to claim 8, wherein, in performing the analysis, the one or more processors are configured to analyze a type of pathology information relating to the lesion diagnosis.

13. The information processing apparatus according to claim 8, wherein, in performing the analysis, the one or more processors are configured to analyze a treatment motion performed by the medical device that acquired the medical image.

14. The information processing apparatus according to claim 1, wherein, in performing the analysis, the one or more processors are configured to:
output the result of the identification; and
after outputting the result of the identification, analyze a motion relating to interpretation of the medical image by a user to acquire the result of the analysis.

15. An image recording apparatus comprising:
one or more processors comprising hardware, wherein the one or more processors are configured to:
acquire a medical image;
perform identification of whether the medical image has a predetermined region;
perform analysis of whether one or more predetermined motions is performed by a medical device that captured the medical image;
perform comparison of a result of the identification and a result of the analysis to determine one of:
coincidence of identification of the medical image as having the predetermined region and performance of the one or more predetermined motions by the medical device that captured the medical image, and
noncoincidence of identification of the medical image as having the predetermined region and performance of the one or more predetermined motions by the medical device that captured the medical image;
generate one of a plurality of tags based on a result of the comparison;
impart the tag generated to the medical image; and
record the medical image to which the tag is imparted and information relating to the result of the comparison.

16. The image recording apparatus according to claim 15, wherein, the one or more processors are configured to:
in response to determining the coincidence, generate a coincidence tag, as the tag; and
in response to determining the noncoincidence, generate a noncoincidence tag, as the tag.

17. The image recording apparatus according to claim 16, wherein the one or more processors are configured to:
in performing the comparison, analyze a degree of the noncoincidence as one of:
one degree of noncoincidence in which the medical image is identified as having the predetermined region and the one or more predetermined motions by the medical device that captured the medical image has not been performed; and
another degree of noncoincidence in which the medical image is not identified as having the predetermined region and the one or more predetermined motions by the medical device that captured the medical image has been performed; and
generate one of a plurality of weighting tags, as the noncoincidence tag, corresponding to the degree of the noncoincidence analyzed.

18. The image recording apparatus according to claim 17, wherein the one or more processors are configured to rank the coincidence tag and non-coincidence tag according to a predetermined standard.

19. The image recording apparatus according to claim 18, wherein the one or more processors are configured to:
change image quality relating to the medical image according to the rank of the tag imparted to the medical image; and
record the medical image, the image quality of which is changed.

20. The image recording apparatus according to claim 16, wherein the one or more processors are configured to only record the medical image imparted with the noncoincidence tag.

21. The image recording apparatus according to claim 17, wherein the one or more processors are configured to only record the medical image imparted with a predetermined tag of the plurality of weighting tags.

22. The image recording apparatus according to claim 15, wherein the one or more processors are configured to change:
change image quality relating to the medical image according to the tag imparted to the medical image; and
record the medical image, the image quality of which is changed.

23. The image recording apparatus according to claim 15, wherein the one or more processors are configured to only record the medical image to which a predetermined tag, of the plurality of tags, is imparted.

24. The image recording apparatus according to claim 15, wherein the one or more processors are configured to:
create a list in which the result of the identification and the result of the analysis are linked; and
record the list together with the medical image corresponding to the list.

25. The image recording apparatus according to claim 15, wherein the one or more processors are configured to not record a medical image to which a predetermined tag, of the plurality of tags, is imparted.

26. The image recording apparatus according to claim 15, wherein the one or more processors are configured to:
set, based on the result of the comparison, the medical image to be a target of additional learning; and
generate a tag for learning target to be imparted to the medical image set to the target of additional learning; and
impart the tag for learning target to the medical image.

27. The image recording apparatus according to claim 26, wherein the one or more processors are configured to execute additional learning of a learning network in an identification apparatus for performing the identification in only the medical image to which the tag for learning target is imparted.

28. The image recording apparatus according to claim 15, wherein the one or more processors are configured to execute additional learning of a learning network in an identification apparatus for performing the identification in only the medical image to which the tag is imparted.

29. The image recording apparatus according to claim 15, wherein the one or more processors are configured to:
    determine whether the medical image to which the tag is imparted satisfies a preset condition; and
    transfer, the medical image to which the tag is imparted determined to satisfy the preset condition to an external recording apparatus.

30. An information processing method comprising:
    acquiring a medical image;
    performing identification of whether the medical image has a predetermined region;
    performing analysis of whether one or more predetermined motions is performed by a medical device that acquired the medical image;
    performing comparison of a result of the identification and a result of the analysis to determine one of:
        coincidence of identification of the medical image as having the predetermined region and performance of the one or more predetermined motions by the medical device that captured the medical image, and
        noncoincidence of identification of the medical image as having the predetermined region and performance of the one or more predetermined motions by the medical device that captured the medical image;
    generating one of a plurality of tags based on a result of the comparison; and
    imparting the tag to the medical image.

31. A non-transitory computer-readable recording medium recording an information processing program, the information processing program causing a computer to execute:
    acquiring a medical image;
    performing identification of whether the medical image has a predetermined region;
    performing analysis of whether one or more predetermined motions is performed by a medical device that acquired the medical image;
    performing comparison of a result of the identification and a result of the analysis to determine one of:
        coincidence of identification of the medical image as having the predetermined region and performance of the one or more predetermined motions by the medical device that captured the medical image, and
        noncoincidence of identification of the medical image as having the predetermined region and performance of the one or more predetermined motions by the medical device that captured the medical image;
    generating one of a plurality of tags based on a result of the comparison; and
    imparting the tag to medical image.

* * * * *